(12) United States Patent
Donaldson et al.

(10) Patent No.: US 6,251,925 B1
(45) Date of Patent: Jun. 26, 2001

(54) THERAPEUTIC BIARYL DERIVATIVES

(75) Inventors: Kelly Horne Donaldson, Durham; Barry George Shearer, Apex; David Edward Uehling, Durham, all of NC (US)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 09/719,595

(22) PCT Filed: Jun. 9, 1999

(86) PCT No.: PCT/EP99/03958

§ 371 Date: Dec. 13, 2000

§ 102(e) Date: Dec. 13, 2000

(87) PCT Pub. No.: WO99/65877

PCT Pub. Date: Dec. 23, 1999

(30) Foreign Application Priority Data

Jun. 13, 1998 (GB) .................................. 9812709

(51) Int. Cl.$^7$ .................. C07C 229/52; C07C 213/79; C07C 213/88; A61K 31/44; A61K 31/19

(52) U.S. Cl. .......... 514/354; 514/344; 514/356; 514/524; 514/539; 514/564; 546/322; 546/321; 546/286; 546/326; 548/252; 558/422; 549/462; 560/42; 562/451

(58) Field of Search ............... 546/322, 326, 546/321, 286; 548/252; 558/422; 549/462; 560/42; 562/451; 514/344, 354, 356, 524, 539, 564

(56) References Cited

U.S. PATENT DOCUMENTS

| 4,478,849 | 10/1984 | Ainsworth et al. .............. 560/34 |
| 4,772,631 | 9/1988 | Holloway et al. ............... 514/539 |

FOREIGN PATENT DOCUMENTS

| 0 400 519 | 12/1990 | (EP) . |
| 0 455 006 | 11/1991 | (EP) . |
| 0 543 662 | 5/1993 | (EP) . |
| WO 95 33724 | 12/1995 | (WO) . |

Primary Examiner—Bernard Dentz
(74) Attorney, Agent, or Firm—Robert H. Brink

(57) ABSTRACT

The present invention relates to therapeutic biaryl derivatives of formula (I), and pharmaceutically acceptable derivatives thereof

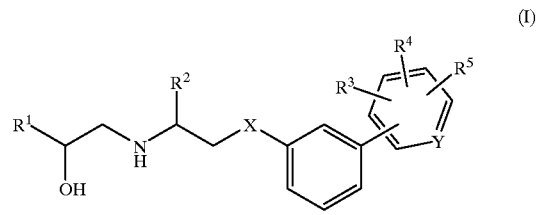

(I)

wherein $R^1$ is a phenyl, naphthyl, pyridyl, thiazolyl, phenoxymethyl, or pyrimidyl group, optionally substituted by one or more substituents selected from the group consisting of halogen, hydroxy, $C_{1-6}$alkoxy, $C_{1-6}$alkyl, nitro, cyano, hydroxymethyl, trifluoromethyl, —$NR^6R^6$, and —$NHSO_2R^6$, where each $R^6$ is independently hydrogen or $C_{1-4}$alkyl; $R^2$ is hydrogen or $C_{1-6}$alkyl; X is oxygen, sulfur, —NH, or —$NC_{1-4}$alkyl; $R^3$ is cyano, tetrazol-5-yl, or —$CO_2R^7$ where $R^7$ is hydrogen or $C_{1-6}$alkyl; $R^4$ and $R^5$ are independently hydrogen, $C_{1-6}$alkyl, —$CO_2H$, —$CO_2C_{1-6}$alkyl, cyano, tetrazol-5-yl, halogen, trifluoromethyl, or $C_{1-6}$alkoxy, or, when $R^4$ and $R^5$ are bonded to adjacent carbon atoms, $R^4$ and $R^5$ may, together with the carbon atoms to which they are bonded, form a fused 5 or 6 membered ring optionally containing one or two nitrogen, oxygen, or sulfur atoms; and Y is N or CH, to processes for their preparation and their use in the treatment of diseases susceptible to ameleoration by treatment with a beta-3 adrenoceptor agonist.

17 Claims, No Drawings

THERAPEUTIC BIARYL DERIVATIVES

This Application is filed pursuant to 35 U.S.C. §371 as a U.S. National Phase Application of International application No. PCT/EP99/03958, filed Jun. 9, 1999 and published as WO 99/65877, Dec. 23, 1999, which claims priority to Great Britain Application No. 9812709.5, filed Jun. 13, 1998.

FIELD OF THE INVENTION

This invention relates to a new class of chemical compounds and to their use in medicine. In particular, the invention relates to biaryl derivatives, methods for their preparation, pharmaceutical compositions containing them, and their use as agonists at atypical beta-adrenoceptors (also known as beta-3-adrenoceptors).

BACKGROUND OF THE INVENTION

Atypical beta-adrenoceptors belong to the family of adrenoceptors which mediate the physiological actions of the hormones adrenaline and noradrenaiine. Such receptors have been described for example by J R S Arch et. al., *Nature*, 309, 163–165 (1984); C Wilson et. al., *Eur. J. Pharrnacol.*, 100, 309–319 (1984); L J Emorine et. al., *Science*, 245, 1118–1121 (1989); and A. Bianchetti et. al. *Br. J. Pharmacol.*, 100, 831–839 (1990).

Phenethanolamine derivatives having activity at atypical beta-adrenoceptors are disclosed in, for example, European Patent Applications EP-A-0455006 and EP-A-0543662.

Sub-types of the adrenoceptors, $\alpha_1$-, $\alpha_2$-, $\beta_1$-, $\beta_2$- and $\beta_3$-(atypical) can be identified on the basis of their pharmacological properties and physiological effects. Chemical agents which stimulate or block these receptors (but not $\beta_3$) are widely used in clinical medicine. More recently, emphasis has been placed upon specific receptor selectivity in order to reduce side effects caused, in part, by interactions with other receptors.

Atypical beta-adrenoceptors are known to occur in adipose tissue and the gastrointestinal tract. Atypical beta-adrenoceptor agonists have been found to be particularly useful as thermogenic anti-obesity agents and as anti-diabetic agents. Compounds having atypical beta-adrenoceptor agonist activity have also been described as being useful in the treatment of hyperglycaemia, as animal growth promoters, as blood platelet aggregation inhibitors, as positive inotropic agents and as antiatheroscierotic agents, and as being useful in the treatment of glaucoma.

SUMMARY OF THE INVENTION

Briefly, in one aspect, the invention therefore provides compounds of Formula (I) and pharmaceutically derivatives thereof:

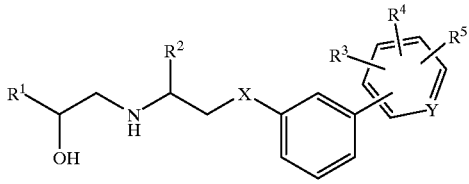

(I)

wherein
$R^1$ is a phenyl, naphthyl, pyridyl, thiazolyl, phenoxymethyl, or pyrimidyl group, optionally substituted by one or more substituents selected from the group consisting of halogen, hydroxy, $C_{1-6}$alkoxy, $C_{1-6}$alkyl, nitro, cyano, hydroxymethyl, trifluoromethyl, —$NR^6R^6$, and —$NHSO_2R^6$, where each $R^6$ is independently hydrogen or $C_{1-4}$alkyl;
$R^2$ is hydrogen or $C_{1-6}$alkyl;
X is oxygen, sulfur, —NH, or —$NC_{1-4}$alkyl;
$R^3$ is cyano, tetrazol-5-yl, or —$CO_2R^7$ where $R^7$ is hydrogen or $C_{1-6}$alkyl;
$R^4$ and $R^5$ are independently hydrogen, $C_{1-6}$alkyl, —$CO_2H$, —$CO_2C_{1-6}$alkyl, cyano, tetrazol-5-yl, halogen, trifluoromethyl, or $C_{1-6}$alkoxy, or, when $R^4$ and $R^5$ are bonded to adjacent carbon atoms, $R^4$ and $R^5$ may, together with the carbon atoms to which they are bonded, forrn a fused 5 or 6 membered ring optionally containing one or two nitrogen, oxygen, or sulfur atoms; and
Y is N or CH.

The compounds of the present invention are of use in medical therapy. Preferably the compounds of this invention are agonists for human beta-3 adrenoceptor ("$\beta_3$"). More preferably, the compounds of this invention are selective agonists for $\beta_3$.

In another aspect, the present invention provides a pharmaceutical formulation comprising a compound of the invention, or a pharmaceutically acceptable derivative thereof, and one or more pharmaceutically acceptable carriers.

In another aspect, the present invention provides a method for the prevention or treatment of clinical conditions or diseases susceptible to amelioration by administration of an atypical beta-adrenoceptor agonist, comprising administration of an effective amount of a compound or composition of this invention, or a pharmaceutically acceptbale derivative thereof.

In a further aspect, the present invention provides the use of a compound of formula (I), or a pharmaceutically acceptable derivative thereof, in the manufacture of a medicament for the treatment of conditions or diseases susceptible to amelioration by administration of an atypical beta-adrenoceptor agonist.

DETAILED DESCRIPTION OF THE INVENTION

As used herein, the terms 'alkyl' and "alkoxy" mean a straight or branched alkyl group or alkoxy group respectively, containing the indicated number of carbon atoms. For example, $C_{1-6}$alkyl means a straight or branched alkyl containing at least 1 and at most 6 carbon atoms.

Preferably, $R^1$ is phenoxymethyl or phenyl optionally substituted by one, two or three substituents selected from halogen, hydroxy, $C_{1-6}$alkoxy, $C_{1-6}$alkyl, nitro, cyano, hydroxymethyl and trifluoromethyl. More preferably, $R^1$ is phenoxymethyl or phenyl substituted by a chlorine, fluorine or bromine atom or a methyl or trifluoromethyl group, which atom or group is preferably located in the meta position. Most preferably $R^1$ represents phenyl substituted by a chlorine atom located in the meta position.

Preferably, $R^2$ is hydrogen or methyl. Most preferably $R^2$ is hydrogen,

Preferably, X is —NH or —$NCH_3$. Most preferably, X is —NH.

Preferably, $R^3$ is —$CO_2H$. Preferably, $R^3$ is bonded to the carbon atom meta or para to the bonded phenyl ring, more preferably the meta position.

Preferably, $R^4$ and $R^5$ are independently hydrogen, methyl, trifluoromethyl, —$CO_2H$ or, where $R^4$ and $R^5$ are bonded to adjacent carbon atoms, $R^4$ and $R^5$, together with the carbon atoms to which they are bonded, form a fused dihydrofuran ring. More preferably, $R^4$ and $R^5$ are independently hydrogen, methyl, or trifluoromethyl. Preferably, at least one of $R^4$ and $R^5$ is hydrogen. Most preferably, both $R^4$ and $R^5$ are hydrogen.

Preferably Y is CH.

Particularly preferred compounds of the invention include those in which each variable in Formula (I) is selected from the preferred groups for each variable. Even more preferable compounds of the invention include those where each variable in Formula (I) is selected from the more preferred or most preferred groups for each variable.

It will be appreciated that the above compounds of Formula (I) may contain optically active centers. The individual, isolated isomers and mixtures thereof, including racemates, are all within the scope of the present invention. Typically, where $R^2$ is $C_{1-6}$alkyl, mixtures of diastereomers of compounds of Formula (I) may be obtained, which are enriched with greater than or equal to 80% by weight of one diastereomer. Particularly preferred compounds of Formula (I) are those wherein the asymmetric carbon atoms in the —CH(OH)— group and the —CH($R^2$)— group are both in the (R)-configuration.

Suitable compounds of Formula (I) of the invention include:

(R)-3'-[[2-[[2-(3-chlorophenyl)-2-hydroxyethyl]amino] ethyl]amino]-[1,1'-biphenyl]-3-carboxylic acid methyl ester;
(R)-3'-[[2-[[2-(3-chlorophenyl)-2-hydroxyethyl]amino] ethyl]amino]-[1,1'-biphenyl]-2,4-dicarboxylic acid dimethyl ester;
(R)-3'-[[2-[[2-(3-chlorophenyl)-2-hydroxyethyl]amino] ethyl]amino]-[1,1'-biphenyl]-2-methyl-5-carboxylic acid methyl ester;
(R)-3'-[[2-[[2-(3-chlorophenyl)-2-hydroxyethyl]amino] ethyl]amino]-[1,1'-biphenyl]-3,4-dicarboxylic acid dimethyl ester;
(R)-3'-[[2-[[2-(3-chlorophenyl)-2-hydroxyethyl]amino] ethyl]amino]-[1,1'-biphenyl]-3-chloro-4-carboxylic acid methyl ester;
(R)-3'-[[2-[[2-(3,5-dichlorophenyl)-2-hydroxyethyl]amino] ethyl]amino]-[1,1'-biphenyl]-3-carboxylic acid methyl ester;
(R)-3'-[[2-[[2-(3,5-dichlorophenyl)-2-hydroxyethyl]amino] ethyl]amino]-[1,1'-biphenyl]-3-carboxylic acid;
(R)-3'-[[2-[[2-(3-chlorophenyl)-2-hydroxyethyl]amino] ethyl]amino]-[1,1'-biphenyl]-3-carboxylic acid;
(R)-3'-[[2-[[2-(3-chlorophenyl)-2-hydroxyethyl]amino] ethyl]amino]-[1,1'-biphenyl]-2,4-dicarboxylic acid 2-methyl ester;
(R)-3'-[[2-[[2-(3-chlorophenyl)-2-hydroxyethyl]amino] ethyl]amino]-[1,1'-biphenyl]-2,4-dicarboxylic acid;
(R)-3'-[[2-[[2-(3-chlorophenyl)-2-hydroxyethyl]amino] ethyl]amino]-[1,1'-biphenyl]-2-methyl-5-carboxylic acid;
(R)-3'-[[2-[[2-(3-chlorophenyl)-2-hydroxyethyl]amino] ethyl]amino]-[1,1'-biphenyl]-3-chloro-4-carboxylic acid;
(R)-3'-[[2-[[2-(3-chlorophenyl)-2-hydroxyethyl]amino] ethyl]amino]-[1,1'-biphenyl]-3,4-dicarboxylic acid;
(R)-3'-[[2-[(2-hydroxy-3-phenoxypropyl)amino]ethyl] amino]-[1,1'-biphenyl]-3-carboxylic acid;
(R)-3'-[2-[[2-(3-chlorophenyl)-2-hydroxyethyl]amino] ethoxy]-[1,1'-biphenyl]-3-carboxylic acid;
3'-[[2R-[[2-(3-chlorophenyl)-2R-hydroxyethyl]amino] propyl]amino]-[1,1'-biphenyl]-4-carboxylic acid;
3'-[[2R-[[2-(3-chlorophenyl)-2R-hydroxyethyl]amino] propyl]amino]-[1,1'-biphenyl]-2-carboxyiic acid;
3'-[[2R-[[2-(3-chlorophenyl)-2R-hydroxyethyl]amino] propyl]amino]-[1,1'-biphenyl]-2,4-dicarboxylic acid;
5-[3-[[2R-[[2-(3-chlorophenyl)-2R-hydroxyethyl]amino] propyl]amino]phenyl]-3-pyridinecarboxylic acid;
2-[3-[[2R-[[2-(3-chlorophenyl)-2R-hydroxyethyl]amino] propyl]amino]phenyl]-3-pyridinecarboxylic acid;
(R)-5-[3-[[2-[[2-(3-chlorophenyl)-2-hydroxyethyl]amino] ethyl]amino]phenyl]-2,3-dihydro-7-benzofurancarboxylic acid;
(R)-5-[3-[[2-[[2-(3-chlorophenyl)-2-hydroxyethyl]amino] ethyl]amino]phenyl]-3-pyridinecarboxylic acid;
(R)-2-[3-[[2-[[2-(3-chlorophenyl)-2-hydroxyethyl]amino] ethyl]amino]phenyl]-4-pyridinecarboxylic acid;
(R)-6-[3-[[2-[[2-(3-chlorophenyl)-2-hydroxyethyl]amino] ethyl]amino]phenyl]-2-pyridinecarboxylic acid;
(R)-3'-[[2-[[2-(3-chlorophenyl)-2-hydroxyethyl]amino] ethyl]amino]-[1,1'-biphenyl]-3-(5-tetrazole);
(R)-3'-[[2-[[2-(3-chlorophenyl)-2-hydroxyethyl]amino] ethyl]amino]-[1,1'-biphenyl]-3-carbonitrile; and pharmaceutically acceptable derivatives thereof.

As used herein, "a pharmaceutically acceptable derivative" means a pharmaceutically acceptable salt, ester, or salt of such ester, which, upon administration to the recipient, is capable of providing (directly or indirectly) a compound of Formula (I) or an active metabolite or residue thereof. It will be appreciated by those skilled in the art that the compounds of Formula (I) may be modified to provide pharmaceutically acceptable derivatives thereof at any of the functional groups in the compounds of Formula (I). Of particular interest as such derivatives are compounds modified at the carboxyl function, hydroxyl functions or at amino groups. It will be appreciated by those skilled in the art that the pharmaceutically acceptable derivatives of the compounds of Formula (I) may be derivatised at more than one position.

Preferred pharmaceutically acceptable derivatives of the compounds of Formula (I) are pharmaceutically acceptable salts thereof. Pharmaceutically acceptable salts of the compounds of Formula (I) include those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic, while not in themselves pharmaceutically acceptable may be useful in the preparation of salts useful as intermediates in obtaining compounds of the invention and their pharmaceutically acceptable acid addition salts. Salts derived from appropriate bases include alkali metal (e.g. sodium), alkaline earth metal (e.g. magnesium), ammonium and $NR_4^+$ (where R is $C_{1-4}$alkyl) salts.

The compounds of Formula (I) act as agonists at atypical beta -adrenoceptors and as such are useful in the treatment of clinical conditions susceptible to amelioration by administration of an atypical beta-adrenoceptor agonist. Such conditions include hyperglycaemia, obesity, hyperlipemia, irritable bowel syndrome and its associated pain, motility dysfunction, excessive gastrointestinal secretion, non-specific diarrhea, neurogenic inflammation, regulation of intraocular pressure, triglyceridemia, diabetes, e.g. non-insulin-dependent diabetes mellitus (NIDDM or Type 2), such as obese NIDDM and non-obese NIDDM, diabetic complications such as retinopathy, nephropathy, neuropathy, cataracts, coronary heart diseases and arteriosclerosis, osteoporosis; and gastrointestinal disorders, particularly inflammatory gastrointestinal disorders. They are also of use in increasing the high-density-lipoprotein (HDL) cholesterol concentration and decreasing the triglyceride concentration in blood serum, especially human blood serum, and are therefore of potential use in the treatment and/or prophylaxis of atherosclerosis. They also may be useful for the treatment of hyperinsulinaemia, depression, muscle wasting, and urinary incontinence. They may also be useful in the preparation of wound-healing medecines. References in this specification to treatment include prophylactic treatment as well as the alleviation of symptoms.

In a further aspect, the invention provides the use of a compound of general Formula (I) or a pharmaceutically acceptable salt or solvate thereof, for the manufacture of a medicament for the treatment of a condition susceptible of amelioration by an atypical beta-adrenoceptor agonist.

While it is possible that, for use in therapy, a compound of the invention may be administered as the raw chemical it is preferable to present the active ingredient as a pharmaceutical formulation. The invention thus further provides a pharmaceutical formulation comprising a compound of Formula (I) or a pharmaceutically acceptable derivative thereof together with one or more pharmaceutically acceptable carriers thereof and, optionally, other therapeutic and/or prophylactic ingredients. The carrier(s) or excipient(s) must be "acceptable" in the sense of being compatible with the other ingredients of the formulation and not deleterious to the recipient thereof.

The compounds for use according to the present invention may be formulated for oral, buccal, parenteral, rectal or transdermal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For buccal administration the compositions may take the form of tablets or lozenges formulated in conventional manner.

The compounds according to the present invention may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g. sterile pyrogen-free water, before use.

The compounds according to the present invention may also be formulated in rectal compositions such as suppositories or retention enemas, e.g. containing conventional suppository bases such as cocoa butter or other glycerides.

In addition to the formulations described previously, the compounds may also be formulated as a depot preparation. Such long acting formulations may be administered by implantation (for example subcutaneously, transcutaneously or intramuscularly) or by intramuscular injection. Thus, for example, the compounds according to the present invention may be formulated with suitable polymeric or hydrophobic materials (for example as an emulsion in an acceptable oil) or ion exchange resins, or as sparingly soluble derivatives, for example, as a sparingly soluble salt.

Suitable therapeutic ingredients which may be formulated with compounds of the invention, together with one or more pharmaceutical carriers or excipients, include ingredients which may be used in the same clinical conditions as those listed herein for atypical beta-adrenoceptor agonists. Such ingredients may include, for example, PPAR-gamma agonists.

A proposed dose of the compounds according to the present invention for administration to a human (of approximately 70 kg body weight) is 0.1 mg to 1 g, preferably to 1 mg to 100 mg of the active ingredient per unit dose, expressed as the weight of free base. The unit dose may be administered, for example, 1 to 4 times per day. The dose will depend on the route of administration. It will be appreciated that it may be necessary to make routine variations to the dosage depending on the age and weight of the patient as well as the severity of the condition to be treated. The precise dose and route of administration will ultimately be at the discretion of the attendant physician.

The compounds of the invention may be prepared by any of the processes known in the art for the preparation of similar compounds. For example, according to a first process (A), compounds of Formula (I) may be prepared from of a compound of Formula (II):

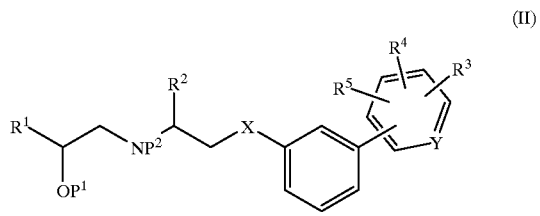

where $P^1$ and $P^2$ are suitable protecting groups for oxygen and nitrogen groups respectively, by deprotection of $P^1$ and $P^2$ under suitable conditions such as treatment with an acid, e.g. aqueous hydrochloric acid in a suitable solvent such as dioxane.

As a further process (B), compounds of Formula (I) may be prepared from other compounds of Formula (I). For instance, a compound of Formula (I) where $R^3$ is $CO_2H$ may be prepared from a corresponding ester by hydrolysis, e.g. base hydrolysis with a reagent such as lithium hydroxide in a solvent such as tetrahydrofuran.

Compounds of Formula (II) where X=NH may be prepared by reaction of a compound of Formula (III) with a compound of Formula (IV):

(III)

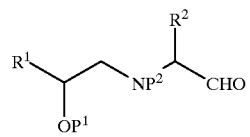

(IV)

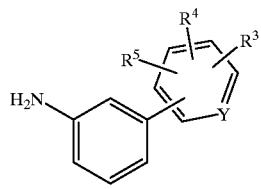

where $P^1$ and $P^2$ are suitable protecting groups for oxygen and nitrogen groups respectively.

Compounds of Formula (II) where $R^3$ is tetrazol-5-yl may be prepared from compounds of Formula (II) where $R^3$ is cyano, by treatment with, for example, trimethylsilyl azide in a solvent such as toluene.

As a yet further process (C), the preparation of compounds of Formula (II), as defined above, followed by step (A) may be combined without purification of intermediate products.

Compounds of Formula (III) are described in WO95/33724 or may be prepared by standard methods described herein.

Compounds of Formula (IV) may be prepared from compounds of Formula (V). Methods of conversion of compounds of Formula (V) to compounds of Formula (IV) are well known and include, but are not limited to, treatment of a compound of Formula (V) with tin(II) chloride in a suitable solvent such as ethyl acetate or stirring under a hydrogen atmosphere in a suitable solvent such as tetrahydrofuran in the presence of a suitable catalyst such as palladium(0) on carbon.

(V)

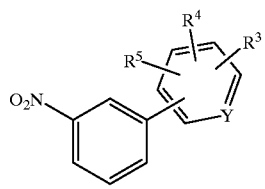

Compounds of Formula (V) may be prepared by reaction of a compound of Formula (VI) with a compound of Formula (VII) according to the method of Thompson, (*J. Org. Chem.* 1984, 49, 5237) where Z is halogen or triflate.

(VI)

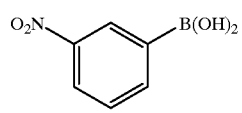

(VII)

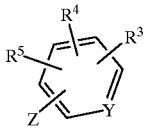

According to another process (D), compounds of Formula (I) may be prepared by reaction of a compound of Formula (VIII) with a compound of Formula (IX) in a suitable solvent such as methyl sulfoxide.

(VIII)

(IX)

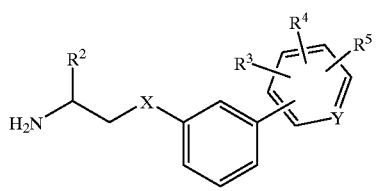

Compounds of Formula (IX) where $X=NH_2$ may be prepared by reaction of compounds of Formula (X) with compounds of Formula (IV), in the presence of a suitable reducing agent followed by removal of $P^2$ using standard methods.

(X)

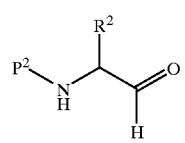

A compound of Formula (IX) may also be prepared from a compound of Formula (XI) in the presence of a suitable reducing agent such as borane in tetrahydrofuran followed by removal of $P^2$ using standard conditions.

(XI)

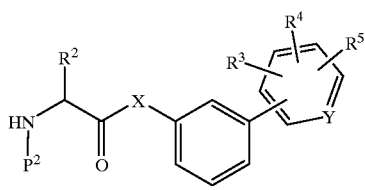

A compound of Formula (XI) where $X=NH_2$ in turn may be prepared by reaction compound of Formula (IV) with a compound of Formula (XII), in the presence of a suitable agent such as 1-(3-dimethylaminopropyl)-3-ethylcarbodiimide hydrochloride.

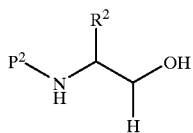
(XII)

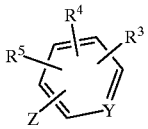
(VII)

A compound of Formula (IX) where X is O may be prepared by the reaction of a compound of Formula (XIII) with a suitable base such as potassium carbonate followed by treatment with a compound of Formula (XIV), where $R^3$ is not $CO_2H$, followed by removal of $P^2$. Referring to Formula (XIII), LG is a leaving group, preferably halogen.

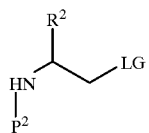
(XIII)

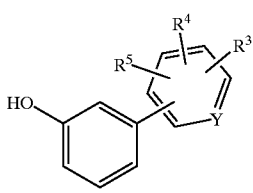
(XIV)

A compound of Formula (XIV) may be prepared by treatment of a compound of Formula (XV), where $R^3$ is not $CO_2H$, with a suitable reagent such as boron tribromide. A compound of Formula (XV) may in turn be prepared by treatment of 3-methoxyphenylboronic acid with a compound of Formula (VII) in the presence of a suitable catalyst according to the method described above.

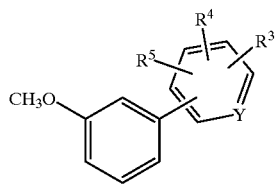
(XV)

Compounds of Formula (XV) may be prepared by reaction of a compound of Formula (XVI) with a compound of Formula (VII) according to the method of Thompson, (J. Org. Chem. 1984, 49, 5237) where Z is halogen or triflate.

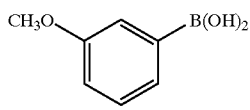
(XVI)

Suitable reducing agents of use in the reactions include hydrogen in the presence of a catalyst, such as a noble metal catalyst, for example palladium, platinum or platinum oxide, Raney-nickel or hydride reducing agents such as borohydrides, for example sodium borohydride, sodium triacetoxyborohydride or sodium cyanoborohydride. Suitable reaction conditions will be readily apparent to those skilled in the art and are further illustrated by the accompanying examples.

The protecting groups used in the preparation of compounds of Formula (I) may be used in conventional manner. See, for example, "Protective Groups in Organic Chemistry", Ed. J. F. W. McOmie (Plenum Press 1973) or "Protective Groups in Organic Synthesis", by Theodora W Greene and P M G Wuts (John Wiley and Sons 1991).

Conventional amino protecting groups may include for example aralkyl groups, such as benzyl, diphenylmethyl or triphenylmethyl groups; and acyl groups such as N-benzyloxycarbonyl or t-butoxycarbonyl. Conventional oxygen protecting groups may include for example alky silyl groups, such as trimethylsilyl, or tert-butyldimethylsilyl; alkylethers such as tetrahydropyranyl, or tert-butyl; or esters such as acetate. Removal of any protecting groups present may be achieved by conventional procedures.

Atypical beta-adrenoceptor agonists are compounds which demonstrate a pharmacological response mediated at atypical beta-adrenoceptors. This activity has been measured as the ability to stimulate lipolysis by rat adipocytes at sub-micromolar concentrations, in a response that is resistant to blockade by standard beta-adrenoceptor blocking drugs such as propranolol.

Another useful means of identifying an atypical beta-adrenoceptor agonist involves the measurement of agonist activity at atypical beta-adrenoceptors in the rat isolated lower oesophagus. Typically in this assay, a compound of general Formula (I) for use according to the present invention has an equipotent molar ratio (EPMR) relevant to isoprenaline of less than 30. The rat oesophagus assay is based upon that described by Ford et. al., Br. J. Pharmacol., 105(suppl.), 235P, 1992. The relative potency of each test compound (EPMR) is compared to isoprenaline as follows:

$$EPMR = \frac{EC_{50} \text{ agonist}}{EC_{50} \text{ isoprenaline}}$$

wherein $EC_{50}$ is the molar concentration of agonist which produces 50% of the maximum possible response for that agonist.

A particularly useful method for determining agonist activity at human atypical beta-adrenoceptors involves the use of Chinese hamster ovarian (CHO) cells transfected with the human beta-3-adrenoceptor according to Method 1. The cell lines may also be transfected with human beta-1- and beta-2-adrenoceptor in a similar manner to provide a method of determining the selectivity of the compounds of the invention at the three receptors.

Method 1-Cell culture

General cell culture guidelines are observed (Fershney, R. A. (1987) Culture of animal cells: A manual of basic technique. VViley-Liss, Inc., N.Y.). A standard cell culture incubator is used (37° C., 5% $CO_2$ in air, 95% relative humidity). H $\beta_3$CHO cells are grown in DMEM/F12 (with pyroxidine.HCl, 15 mM HEPES, L-glutamine), supplanted with 10% heat-inactivated FBS, 500 μg/ml G418, 2 mM L-glutamine, 100 units penicillin G and 100 μg streptomycin sulfate. One confluent flask of cells is trypsinised and resuspended in the above medium at a concentration of 30–40,000 cells/100 μl and plated into 96-well flat bottom plates. The cells are then used for assay within 18–24 hours.

The medium is aspirated from each well, and replaced with 180 μl DMEM/F12 with 500 mM IBMX. Antagonists, if required, are added at this stage. The plate is then placed back in the incubator for 30 min. Drugs are then added to the wells (20 μl, 100 x required final concentration) for 60 min. Responses were determined by measuring cAMP levels of a 20 ul sample of extracellular media using a scintillation proximity based radio-immunoassay (NEN Flashplates). CHO-6CRE-iuciferase cell lines which stably express $h\beta_3$ receptors are seeded at 30,000 cells/well for 24 hr in DMEM/F12 containing 10% FBS. Media is removed from the cells and replaced with DMEM/F12 buffer (180 μl) containing 300 mM IBMX and 1 mM ascorbic acid for 30 min prior to addition of compound. Vehicle or agonist (20 μl) is added and incubated at 37° C. for 60 minutes. At the end of the incubation period, samples of extracellular media are removed for direct assay in cAMP Flashplates (NEN).

As used herein, a compound is considered to be an agonist for $h\beta_3$ if the compound stimulates the accumulation of extracellular cAMP with CHO-6CRE-luciferase cells expressing $h\beta_3$. Preferably, the compounds of this invention have an $EC_{50}$ of at most 100 nM at $h\beta_3$. More preferably, the compounds of this invention have an $EC_{50}$ of at most 1 nM at $h\beta_3$. The relative potency of a $h\beta_3$ agonist may be compared to its potency for stimulating the accumulation of extracellular cAMP with CHO-6CRE-luciferase cells expressing $h\beta_2$ and $h\beta_1$. Preferably, the compounds of this invention are at least 100 times more potent at $h\beta_3$ than at $h\beta_2$ or $h\beta_1$. More preferably, the compounds of this invention are at least 300 times more potent at $h\beta_3$ than at $h\beta_2$ or $h\beta_1$. The compounds of Examples 9, 10, 11, 12, 13, 14, 16, 17, 20, 21, 22, 23, and 24 have an $EC_{50}$ of at most 100 nM at $h\beta_3$ and are at least 100 times more potent at $h\beta_3$ than at $h\beta_2$ or $h\beta_1$. Examples 10, 13. 16, 20, and 24 have an $EC_{50}$ of at most 1 nM and are greater than 300-fold selective at $h\beta_2$ and $h\beta_1$.

EXAMPLES

The invention is further illustrated by the following intermediates and examples. All temperatures are in degrees centigrade. HPLC characterization was carried out where specified using a Dynamax-60A C18 83-201-C, 25 cm×4.6 mm column, eluting with 5–40% $CH_3CN$ in $H_2O$ with 0.1% TFA buffer, with a program time of 30.0 min and flow rate of 1.5 mL/min). Retention times are expressed as $t_r$ in minutes. Optical rotation values are expressed as $[\alpha]_D$ values. Mass spectra (ms) were obtained using electrospray (positive or negative ion) analysis. $^1$H nmr was carried out in deuterated choloroform, unless otherwise indicated.

Intermediate 1

Methyl 4-bromo-2-chlorobenzoate

To anhydrous methanol (45 mL) was added acetyl chloride (1.9 mL) over 2 min. The mixture, which became slightly exothermic and evolved gas, was stirred for 15 min. 4-Bromo-2-chlorobenzoic acid (3.0 g) was added in one portion and the mixture was heated at gentle reflux for 16 h. The mixture was allowed to cool to room temperature and the solvent was removed with a rotary evaporator. The residue was partitioned between saturated aqueous sodium bicarbonate and diethyl ether. The organic layer was separated, dried over sodium sulfate, filtered and concentrated to afford the title compound as a white solid (2.89 g).

n.m.r. δ values include 3.90 (s, 3 H), 7.44 (dd, 1 H), 7.62 (d, 1 H), 7.70 (d, 1 H). m.p. 28–30° C.

Similarly prepared were:

Intermediate 2

Methyl 3-bromo4-methylbenzoate as a pale yellow oil (2.61 g);

n.m.r. δ values include 2.40 (s, 3 H), 3.90 (s, 3 H), 7.25 (d, 1 H), 7.80 (d, 1 H), 8.15 (s, 1 H), from 3-bromo4-methylbenzoic acid (2.63 g) and acetyl chloride(1.8 mL).

Intermediate 3

Dimethyl 4-bromophthalate as a paie yellow oil (3.1 g);

n.m.r. (DMSO-$d_6$) δ values include 3.79 (s, 3 H), 3.80 (s, 3 H), 7.68 (d, 1 H), 7.86 (dd, 1 H), 7.89 (d, 1 H), from 4-bromophthalic acid (3.0 g) and acetyl chloride (1.8 mL) in anhydrous methanol (50 mL).

Intermediate 4

Dimethyl 4-bromoisophthalate as a white solid (3.09 g), n.m.r. δ values include 3.92 (s, 3 H), 3.94 (s, 3 H), 7.73 (d, 1 H), 7.94 (dd, 1 H), 8.42 (d, 1 H), from 4-bromoisophthalic acid (3.0 g) and acetyl chloride (1.8 mL) in anhydrous methanol (50 mL).

Intermediate 5

3-Bromo-5-pyridinecarboxylic acid methyl ester as a pale yellow solid (2.97 g);

n.m.r. (DMSO-$d_6$) δ values include 3.89 (s, 3 H), 8.44 (s, 1 H), 8.97 (s, 1 H), 9.04 (s, 1 H), from 3-bromo-5-pyridinecarboxylic acid (3.00 g).

Intermediate 6

2-Hydroxy-3-pyridinecarboxylic acid methyl ester as a white solid (1.58 g), n.m.r. (DMSO-$d_6$) δ values include 3.71 (s, 3 H), 6.25 (t, 1 H), 7.64 (dd, 1 H), 8.04 (dd, 1 H), 12.08 (bs, 1 H), from 2-hydroxy-3-pyridinecarboxylic acid (2.50 g).

Intermediate 7

2-(Trifluoromethanesulfonyl)oxy-3-pyridinecarboxylic acid methyl ester

To a stirred, cooled (−78° C.) solution of 2-hydroxy-3-pyridinecarboxylic acid methyl ester (1.12 g) in dichloromethane was added diisopropylamine (1.04 g) dropwise. The mixture was stirred for 20 min and then trifluoromethanesulfonic anhydride (2.18 g) was added dropwise. After 30 min, the mixture was quenched with water, warmed to room temperature and extracted with dichloromethane. The organic layer was dried over magnesium sulfate. The solvent was removed under reduced pressure and the residue was chromatographed on silica gel eluting with 1:4 ethyl acetate in hexane to provide the title compound (1.66 g) as a white solid. Electrospray MS (positive ion): (M+H) 307.

n.m.r. (DMSO-$d_6$) δ values include 3.90 (s, 3 H), 7.78 (dd, 1 H), 8.58 (dd, 1 H), 8.69 (dd, 1 H).

Intermediate 8

2-Bromo4-pyridinecarboxylic acid ethyl ester

To a suspension of 2-bromo4-pyridine carboxylic acid (prepared according to the method of Ashimori, *Chem. Pharm. Bull.* 38 (9) 2446–2458 (1990)) in 2:1 toluene: absolute ethanol (45 mL) was added sulfuric acid (0.75 mL). The mixture was heated at reflux for 16 h. The mixture was poured into saturated aqueous sodium bicarbonate and extracted with chloroform (3 times). The combined chloroform extracts were dried over magnesium sulfate, filtered and concentrated afforded the crude product as a yellow oil. Purification by silica gel chromatography eluting with 9:1 hexane:ethyl acetate to afford the title compound (900 mg) as a clear, colorless oil.

n.m.r. δ values include 1.39 (t, 3 H), 4.40 (q, 2 H), 7.79 (d, 1 H), 8.02 (s, 1 H), 8.50 (d, 1 H).

Intermediate 9

2-Bromo-6-pyridine-carboxylic acid

To deionized water (75 mL) was added 2-bromo-6-methylpyridine (5.0 g) and potassium permanganate (4.74 g). After refluxing for 1 h another portion of potassium permanganate (4.74 g) in deionzied water (75 mL) was added. The mixture was heated at reflux for an additional 5 h and filtered through ceiite. The filtrate was acidified with 6 N hydrochloric acid and the product precipitated as a white solid. The solid was collected by suction filtration and the filtrate was extracted with ethyl acetate, dried over sodium sulfate, filtered and concentrated to yield more title product (total 2.65 g).

m.p. 189–191° C.

Intermediate 10

2-Bromo-6-pyridine-carboxylic acid ethyl ester

Sulfuric acid (1.46 mL) was added to a mixture of 2-bromo-6-pyridine-carboxylic acid, ethanol (15 mL) and toluene (30 mL). The reaction heated to reflux for 16 h. The mixture was partitioned between chloroform and a saturated aqueous solution of sodium bicarbonate. The aqueous layer was extracted with chloroform (2 x) and the combined organic layers were dried over sodium sulfate, filtered and concentrated to yield a cloudy orange oil. The oil was purified by silica gel chromatography with 9:1 hexane:ethyl acetate. The title product was obtained as an oily white solid (1.31 g).

n.m.r.($CD_3OD$) δ values include 1.39 (t, 3 H), 4.41 (q, 2 H), 7.79 (d, 2 H), 7.85 (t, 1 H), 8.08 (d, 1 H).

Intermediate 11

3'-Nitro-[1,1'-biphenyl]-4-carboxylic acid methyl ester

To a stirred mixture of methyl 4-bromobenzoate (1.00 g) and 3-nitrophenylboronic acid (800 mg) in dioxane (20 mL) was added tetrakis(triphenylphosphine)palladium(0) (165 mg) and solid sodium carbonate (710 mg). The mixture was heated at 85° C. overnight, cooled to room temperature and partitioned between dichloromethane (100 mL) and 2 M aqueous sodium carbonate (50 mL) containing concentrated ammonium hydroxide (5 mL). The aqueous layer was further extracted twice with dichioromethane. The combined organic layers were washed with brine, dried over magnesium sulfate and concentrated under reduced pressure. The residue was absorbed onto silica and chromatographed on silica gel eluting with 6:94 ethyl acetate in hexane to provide the title compound (198 mg) as a white solid n.m.r. (DMSO-$d_6$) δ values include 3.88 (s, 3 H), 7.79 (t, 1 H), 7.95 (dd, 2 H), 8.07 (dd, 2 H), 8.24 (m, 21 H), 8.504 (t, 1 H).

Similarly prepared were:

Intermediate 12

3'-Nitro-[1,1'-biphenyl]-2-carboxylic acid methyl ester as a white solid (1.81 g);

n.m.r. (DMSO-$d_6$) δ values include 3.61 (s, 3 H), 7.51 (d, 1 H), 7.58 (t, 1 H), 7.69 (m, 3 H), 7.88 (d, 1 H), 8.24 (d, 1 H); from methyl 2-bromobenzoate (1.53 g), tetrakis(triphenylphosphine)palladium(0) (270 mg) and 3-nitrophenylboronic acid (1.44 g).

Intermediate 13

3'-Nitro-[1,1'-biphenyl]-3-carboxylic acid methyl ester as a brown solid (2.28 g);

n.m.r. δ values include 3.96 (s, 3 H), 7.57 (t, 1 H), 7.64 (t, 1 H), 7.81 (d, 1 H), 7.94 (d,1 H), 8.09 (d, 1 H), 8.23 (dd, 1 H), 8.30 (s, 1 H), 8.48 (t, 1 H), m.p., 88–90° C.; from methyl 3-bromobenzoate (2.0 g), tetrakis(triphenylphosphine)palladium(0) (348mg) and 3-nitrophenylboronic acid (1.9 g).

Intermediate 14

3-(3-Nitrophenyl)-5-pyridinecarboxylic acid methyl ester
Intermediate 14 was prepared as a tan solid (296 mg);

Assay Found: C 60.61; H 3.93; N 10.78% $C_{13}H_{10}N_2O_4$ requires C 60.47; H 3.90; N 10.85%; from 3-bromo-5-pyridinecarboxylic acid methyl ester (1.00 g) and 3-nitrophenylboronic acid (785 mg) tetrakis (triphenylphosphine)palladium(0) (164 mg).

Intermediate 15

2-(3-Nitrophenyl)-3-pyridinecarboxylic acid methyl ester as a tan solid (301 mg);

n.m.r. (DMSO-$d_6$) δ values include 3.69 (s, 3 H), 7.75 (dd, 1 H), 7.94 (dd, 1 H), 8.29 (m, 3 H), 8.86 (dd, 1 H); from 2-(trifluoromethanesulfonyl)oxy-3-pyridinecarboxylic acid methyl ester (506 mg) 3-nitrophenylboronic acid (325 mg) and tetrakis-(triphenylphosphine)palladium(0) (70 mg).

Intermediate 16

3'-Nitro-[1,1'-biphenyl]-3,4-dicarboxylic acid dimethyl ester as a brown solid (1.6 g);

n.m.r. δ values include 3.93 (s, 3 H), 3.94 (s, 3 H), 7.65 (t, 1 H), 7.78 (dd, 1 H), 7.86 (d, 1 H), 7.92–7.95 (m, 2 H), 8.26 (dd, 1 H), 8.46 (t, 1 H); from dimethyl 4-bromophthalate (1.80 g), tetrakis(triphenylphosphino) palladium(0) (246 mg) and 3-nitrophenylboronic acid (1.3 g)

Intermediate 17

3'-Nitro-[1,1'-biphenyl]-3-chloro-4-carboxylic acid methyl ester as a brown solid (2.03 g);

n.m.r. δ values include 3.96 (s, 3 H), 7.56 (dd, 1 H), 7.65 (t, 1 H), 7.71 (d, 1 H), 7.91 (d, 1 H), 7.97 (d, 1 H), 8.27 (d, 1 H), 8.47 (m, 1 H); from methyl 4-bromo-2-chlorobenzoate (2.0 g), tetrakis(triphenylphosphino)palladium(0) (299 mg) and 3-nitrophenylboronic acid (1.6 g).

Intermediate 18

3'-Nitro-[1,1'-biphenyl]-2-methyl-5-carboxylic acid methyl ester as a tan solid (605 mg);

Assay found C, 66.36, H, 4.87, 5.15 $C_{15}H_{13}N_1O_4$ requires C, 66.41, H, 4.83, N, 5.16; from methyl 3-bromo4-methylbenzoate (2.3 g) in toluene (28 mL), tetrakis (triphenylphosphino)palladium(0) (381 mg) and 3-nitrophenylboronic acid (2.03 g) in methanol (7 mL).

Intermediate 19

3'-Nitro-[1,1'-biphenyl]-2,4-dicarboxylic acid dimethyl ester as a tan solid (880 mg);

Electrospray MS (positive ion): (M+Na) 338; from dimethyl 4-bromoisophthalate (1.26 g), 3-nitrophenylboronic acid (795 mg) and tetrakis(triphenylphosphine)palladium(0) (167 mg).

Intermediate 20

5-(3-Nitrophenyl)-2,3-dihydro-7-benzofurancarboxylic acid methyl ester as a pale yellow solid (650 mg);

m.p. 53–57 ° C.; from 5-bromo-2,3-dihydro-7-benzofurancarboxylic acid methyl ester (1.0 g), tetrakis (triphenylphosphino)palladium(0) (103 mg), 2 M sodium carbonate (7.0 mL) and 3-nitrophenylboronic acid (741 mg) in methanol (5 mL).

Intermediate 21

3-(3-Nitrophenyl)-5-pyridinecarboxylic acid ethyl ester as a pale yellow solid (400 mg);

n.m.r. δ values include 1.5 (t, 3 H), 4.5 (q, 2 H), 7.75 (t, 1 H), 8.0 (d, 1 H), 8.3 (d, 1 H), 8.6–8.5 (m, 2 H), 9.0 (s, 1 H), 9.3 (s, 1 H); from 3-bromo-5-pyridine carboxylic acid ethyl ester (985 mg) in toluene (15 mL), tetrakis (triphenylphosphino)palladium(0) (161 mg) and 3-nitrophenylboronic acid (860 mg).

Intermediate 22

2-(3-Nitrophenyl)-4-pyridinecarboxylic acid ethyl ester as a white solid (355 mg);

Electrospray MS (positive ion): (M+H) 272.8; from 2-bromo4-pyridinecarboxylic acid ethyl ester (900 mg), tetrakis(triphenylphosphine)paliadium (136 mg), and 3-nitrophenylboronic acid (783 mg).

Intermediate 23

Methyl 3-(3-methoxyphenyl)-benzoate as a clear colorless liquid (3.34 g);

$^1$H NMR δ values include 3.86 (s, 3 H), 3.93 (s, 3 H), 6.91 (dd, 1 H), 7.13 (s, 1 H), 7.76 (d, 1 H), 8.00 (d, 1 H), 8.26 (s, 1 H) from methyl 3-bromobenzoate (5.82 g), tetrakis(triphenylphosphine)palladium (1.0 g) and 3-methoxyphenylboronic acid (5.0 g).

Intermediate 24

3'-Nitro-[1,1'-biphenyl]-3-carbonitrile as a yellow solid (1.96 g), m.p. 169–173° C.; from 3-bromobenzonitrile (2.0 g) in toluene (20 mL), 3-nitrophenylboronic acid (2.2 g), and tetrakis(triphenylphosphine)palladium(0) (381 mg) in methanol (5 mL).

Intermediate 25

6-(3-nitrophenyl)-2-pyridine-carboxylic acid methyl ester and 6-(3-nitrophenyl)-2-pyridine-carboxylic acid ethyl ester as a yellow solid (289 mg) judged by n.m.r. to be 2.7:1 mixture of ethyl: methyl esters;

n.m.r δ values include 1.47 (t, 2.9 H), 4.04 (s, 0.8 H), 4.50 (q, 1.46 H), 7.67 (t, 1 H), 7.97–7.99 (m, 2 H), 8.10–8.16 (m, 1 H), 8.29 (d, 1 H), 8.43–8.48 (m, 1 H), 8.86–8.87 (m, 1 H); from 2-bromo-6-pyridine-carboxylic acid ethyl ester (1.2 g) in toluene (20 mL), tetrakis(triphenylphosphine) palladium (0) (181 mg), 2 M aqueous sodium carbonate (3.3 mL) , and 3-nitrophenylboronic acid (1.0 g) in methanol (5 mL).

Intermediate 26

3'-hydroxy-[1,1'-biphenyl]-3-carboxylic acid methyl ester

To a –78° C. solution of methyl 3-(3-methoxyphenyl)-benzoate (1.48 g) in anhydrous methylene chloride (16 mL) was added dropwise a solution of boron tribromide in methylene chloride (1.0 M, 16.3 mL). The mixture was stirred at –78° C. for 30 min, allowed to warm to 0° C., and stirred for 2 h. The mixture was quenched by addition of saturated aqueous sodium bicarbonate (50 mL), and diluted with methylene chloride (50 mL). The mixture was placed in a separatory funnel, and the organic layer was separated, dried over sodium sulfate, filtered and concentrated to give the crude product. Purification by silica gel chromatography (eluting with 5:1 hexanes/ethyl acetate) afforded the title compound (769 mg) as a pale yellow oil.

NMR δ values include 3.94 (s, 3 H), 6.84 (d, 1 H), 7.09 (s, 1 H), 7.18 (d, 1 H), 7.31 (t, 1 H), 7.49 (t, 1 H), 7.75 (d, 1 H), 8.01 (d, 1 H), 8.25 (s, 1 H).

Intermediate 27

3'-Nitro-biphenyl-3-(1 H-5-tetrazole)

To a stirred mixture of 3'-nitro-[1,1'-biphenyl]-3-carbonitrile (800 mg) and trimethylsilyl azide (823 mg) in toluene (10 mL) was added dimethyltin oxide (59.3 mg). The reaction was heated to 100° C. overnight. The mixture was concentrated, diluted with methanol (5 mL) and concentrated again. The mixture was partitioned between a saturated solution of sodium bicarbonate and ethyl acetate. The organic layer was extracted again with a sodium bicarbonate solution and the combined aqueous layers were acidified with 1 N hydrochloric acid and extracted with ethyl acetate. The combined organic extracts were then dried over magnesium sulfate, filtered and concentrated to yield a white solid (377 mg).

m.p. 271–273 ° C.

Intermediate 28

3'-Amino-[1,1'-biphenyl]-3-carboxylic acid methyl ester

To a stirred solution of 3'-nitro-[1,1'-biphenyl]-3-carboxylic acid methyl ester (4.47 g) in anhydrous tetrahydrofuran (125 mL) under a blanket of nitrogen was added 10% palladium on activated charcoal (860 mg). The reaction was evacuated and placed under a hydrogen atmosphere and stirred overnight. The reaction mixture was filtered through Celite and the solvent was removed under reduced pressure to yield a gray oil (4.4 g). The residue was chromatographed on silica eluting with 3:1 hexane:ethyl acetate. Concentration of the appropriate fractions provided the title compound as a white solid (3.5 g).

n.m.r. δ values include 3.83 (s, 2 H), 3.93 (s, 3 H), 6.70 (d, 1 H), 6.93 (d, 1 H), 7.00 (d, 1 H), 7.25–7.21 (m, 1 H), 7.47 (t, 1 H), 7.73 (d,1 H), 7.98 (d, 1 H), 8.23 (d, 1 H)

Similarly prepared were:

Intermediate 29

3'-Amino-[1,1'-biphenyl]-4-carboxylic acid methyl ester as a pale yellow solid (170 mg);

Electrospray MS (positive ion): (M+H) 228; from 3'-nitro-[1,1'-biphenyl]-4-carboxylic acid methyl ester (196 mg).

Intermediate 30

3'-Amino-[1,1'-biphenyl]-2-methyl-5-carboxylic acid methyl ester as a white crystalline solid (572 mg);

Electrospray MS (positive ion): (M+H) 242.5; from 3'-nitro-[1,1'-biphenyl]-2-methyl-5-carboxylic acid methyl ester (605 mg).

Intermediate

3'-Amino-[1,1'-biphenyl]-2-carboxylic acid methyl ester as a pale yellow solid (910 mg);

n.m.r. (DMSO-$d_6$) δ values include 3.58 (s, 3 H), 5.13 (s, 2 H), 6.38 (d, 1 H), 6.51 (m, 2 H), 7.02 (t, 1 H), 7.40 (m, 2 H), 7.58 (m, 2 H); from 3'-nitro-[1,1'-biphenyl]-2-carboxylic acid methyl ester (1.05 g).

Intermediate 32

5-(3-Aminophenyl)-3-pyridinecarboxylic acid ethyl ester as a pale yellow solid (19.9 mg);

n.m.r. δ values include 1.42 (t, 3 H), 4.43 (q, 2 H), 6.75 (dd, 1 H), 6.90 (t, 1 H), 6.98 (d, 1 H), 8.43 (t, 1 H), 8.95 (d, 1 H), 9.16 (d, 1 H); from 5-(3-nitrophenyl)-3-pyridinecarboxylic acid ethyl ester (100 mg).

Intermediate 33

3'-Amino-[1,1'biphenyl]-2,4-dicarboxylic acid dimethyl ester (458 mg), n.m.r. (DMSO-$d_6$) δ values include 3.64 (s, 3 H), 3.88 (s, 3 H), 5.21 (s, 2 H), 6.41 (d, 1 H), 6.52 (s, 1 H), 6.56 (d, 1 H), 7.06 (t, 1 H), 7.54 (d, 1 H), 8.10 (d, 1 H), 8.17 (s, 1 H); from 3'-nitro-[1,1'biphenyl]-2,4-dicarboxylic acid dimethyl ester (556 mg).

Intermediate 34

5-(3-Aminophenyl)-3-pyridinecarboxylic acid methyl ester (187 mg);

n.m.r. (DMSO-$d_6$) δ values include 3.91 (s, 3 H), 5.28 (s, 2 H), 6.64 (m, 1 H), 6.89 (m, 2 H), 7.15 (t, 1 H), 8.34 (s, 1 H), 9.02 (s, 2 H); from 5-(3-nitrophenyl)-3-pyridinecarboxylic acid methyl ester (220 mg).

Intermediate 35

3'-Amino-[1,1'-biphenyl]-3-carbonitrile as a yellow oil (229 mg);

n.m.r. δ values include 3.80 (bs, 2 H), 6.72 (dd, 1 H), 6.84 (s,1 H), 6.92 (d, 1 H), 7.22–7.26 (m, 2 H), 7.50 (t, 1 H), 7.59 (d, 1 H), 7.76 (d, 1 H), 7.82 (s, 1 H); from 3'-nitro-[1,1'-biphenyl]-3-carbonitrile (430 mg).

Intermediate 36

5-(3-Aminophenyl)-4-pyridinecarboxylic acid ethyl ester

To a solution of 5-(3-nitrophenyl)-4-pyridinecarboxyiic acid ethyl ester in ethyl acetate (20 mL) was added tin(II) chloride (1.47 g). The mixture was heated at 80° C. for 45 min, then allowed to cool to ambient temperature. The mixture was poured into ice and saturated aqueous sodium bicarbonate was added until the mixture attained a pH of approximately 7. Celite and ethyl acetate were added, and the mixture was stirred for 10 min. The mixture was filtered and placed in a separatory funnel. The organic layer was separated, dried over sodium sulfate, filtered and concentrated to yield the crude product. Purification by silica gel chromatography (4:1 hexane: ethyl acetate) afforded the title compound as an orange oil (216 mg).

n.m.r. δ values include 1.42 (t, 3 H), 4.43 (q, 2 H), 6.86 (d, 1 H), 7.29 (t, 1 H), 7.44 (d, 1 H), 7.51 (s, 1 H), 7.78 (d, 1 H), 8.26 (s, 1 H), 8.80 (d, 1 H).

Similarly prepared were:

Intermediate 37

3'-Amino-[1,1'-biphenyl]-3-chloro-4-carboxyiic acid methyl ester (788 mg);

n.m.r. δ values include 3.93 (s, 3 H), 6.72 (d, 1 H), 6.88 (s, 1 H), 6.96 (d, 1 H), 7.25 (m, 1 H), 7.49 (dd, 1 H), 7.64 (d, 1 H), 7.89 (d, 1 H); from 3'-nitro-[1,1'-biphenyl]-3-chloro-4-carboxylic acid methyl ester (1.0 g) and tin (II) chloride (3.9 g).

Intermediate 38

2-(3-Aminophenyl)-3-pyridinecarboxylic acid methyl ester (275 mg);

n.m.r. (DMSO-$d_6$) δ values include 3.65 (s, 3 H), 5.19 (s, 2 H), 6.58 (dt, 2 H), 6.76 (s, 1 H), 7.05 (t, 1 H), 7.44 (dd, 1 H), 8.02 (d, 1 H), 8.73 (d, 1 H); from 2-(3-nitrophenyl)-3-pyridinecarboxylic acid methyl ester (293 mg) and 10% Pd/C (30 mg).

Intermediate 39

3'-Amino-[1,1'-biphenyl]-3,4-dicarboxylic acid dimethyl ester (680 mg);

n.m.r. (DMSO-$d_6$) δ values include 3.77 (s, 2 H), 3.91 (s, 3 H), 3.92 (s, 3 H), 6.70 (m, 1 H), 6.89 (s, 1 H), 6.97 (d, 1 H), 7.21 (d, 1 H), 7.69 (m, 1 H), 7.79 (d, 1 H), 7.85 (m, 1 H); from 3'-nitro-[1,1'-biphenyl]-3,4-dicarboxylic acid dimethyl ester (0.8 g) and 10% Pd/C (560 mg) in tetrahydrofuran (30 mL).

Intermediate 40

5-(3-Aminophenyl)-2,3-dihydro-7-benzofurancarboxyiic acid methyl ester 5-(3-Nitrophenyl)-2,3-dihydro-7-benzofurancarboxylic acid methyl ester (650 mg) and tin(II) chloride (2.3 g) in ethyl acetate (28 mL) were heated at 70° C. for 16 h. The mixture was allowed to cool and poured onto ice. The pH was adjusted to 7–8 by addition of saturated aqueous sodium bicarbonate, and the mixture was extracted with ethyl acetate. The organic layer was washed with brine, treated with charcoal and dried over sodium sulfate. Filtration and removal of solvent afforded the title compound as an oil (470 mg). Electrospray MS (positive ion): (M+H) 270.4.

Similarly prepared were:

Intermediate 41

Amino-[1,1'-biphenyl]-3-(1 H-5-tetrazole) as a light brown oil (57 mg);

n.m.r. (CD$_3$OD) δ values include 6.75 (d, 1 H), 7.02–7.07 (m, 2 H), 7.20 (t,1 H), 7.54 (t,1 H), 7.69 (d, 1 H), 7.96 (d, 1 H), 8.25 (s, 1 H); from 3'-Nitro-[1,1'-biphenyl]-3-(1 H-5-tetrazole) (371 mg) and tin(II) chloride (1.57 g).

Intermediate 42

6-(3-aminophenyl)-2-pyridine-carboxylic acid methyl ester and 3-(3-aminophenyl)-2-pyridine-carboxylic acid ethyl ester as a brown oil (126 mg) believed to be a 1:2.5 mixture of the methyl and ethyl esters;

Electrospray MS (positive ion); (M+H) 229.2 and 243.2; from 6-(3-nitrophenyl)-2-pyridine-carboxylic acid methyl ester and 6-(3-nitrophenyl)-2-pyridine-carboxylic acid ethyl ester (280 mg) and tin(II) chloride (1.16 g).

Intermediate 43

Methyl 3'-[2-[[(tert-butoxy)carbonyl]amino]ethoxy]-[1,1'-biphenyl]-3-carboxylate A mixture of 3'-hydroxy-[1,1'-biphenyl]-3-carboxylic acid methyl ester (667 mg) and 2-bromo-1-[(tert-butoxycarbonyl)amino]ethane (980 mg) in N,N-dimethylformamide (15 mL) was treated with potassium carbonate (2.0 g). The mixture was stirred at room temperature for 30 min, and heated to 50° C. in an oil bath for 14 h. Additional bromide (396 mg) was added and the mixture was heated an additional 36 h. The mixture was cooled to room temperature and partitioned between 1:1 hexane ethyl acetate and water. The organic layer was separated, washed with water, dried over sodium sulfate, filtered and concentrated to give the crude product. Purification by silica gel chromatography (eluting with 5:1 hexane/ethyl acetate) afforded the title compound as a colorless oil (826 mg).

NMR δ values include 1.44 (s, 9 H), 3.56 (m, 2 H), 3.93 (s, 3 H), 4.07–4.11 (m, 2 H), 5.01 (s, 1 H), 6.89–6.91 (m, 1 H), 7.13 (s, 1 H), 7.36 (t, 1 H), 7.49 (t, 1 H), 7.75 (d, 1 H), 8.01 (d, 1 H), 8.24 (s, 1 H).

Intermediate 44

Methyl 3'-[(2-[[(tert-butoxy)carbonyl]amino]acetylamino)]-[1,1'-biphenyl]-3-carboxylate To a mixture of 3'-amino-[1,1'-biphenyl]-3-carboxylic methyl ester (1.14 g) and N-(tert-butoxycarbonyl)glycine (0.879 g) in methylene chloride (20 mL) was added 1-(3-dimethylaminopropyl)-3-ethylcarbodiimide hydrochloride (1.20 g). The mixture was stirred for 3 h at room temperature, then washed twice with 1 N aqueous HCl, twice with saturated aqueous sodium bicarbonate and once with brine. The mixture was dried over sodium sulfate, filtered and concentrated to give a foam. Purification by silica gel chromatography eluting with 7:3 hexane/ethyl acetate gave 1.6 g of the title compound as a colorless oil. Electrospray MS (positive ion): (M+Na) 407.0.

Intermediate 45

Methyl 3'-[(2-[[(tert-butoxy)carbonyl]amino]ethyl)amino]-[1,1'-biphenyl]-3-carboxylate To methyl 3'-[(2-[[(tert-butoxy)carbonyl]amino]acetylamino)]-[1,1'-biphenyl]-3-carboxylate (1.6 g) 0° C. was added a 1.0 M solution of borane in tetrahydrofuran (30 mL). The mixture was warmed to room temperature and stirred for 3 h. The mixture was quenched with saturated aqueous sodium bicarbonate and concentrated to leave a cloudy liquid that was partitioned between ethyl acetate and saturated aqueous sodium bicarbonate. The separated organic layer was washed with brine, dried over sodium sulfate, filtered and concentrated to give the crude product. Purification by silica gel chromatography provided the title compound (740 mg). Electrospray MS (positive ion): M+Na 393.0

Intermediate 46

Methyl-3'-[(-2-aminoethyl)amino]-[1,1'-biphenyl]-3-carboxylate

To methyl-3'-[(2-[[(tert-butoxy)carbonyl]amino]ethyl)amino]-[1,1'-biphenyl]-3-carboxylate (730 mg) was added 4 N HCl in dioxane (20 mL) and the mixture was stirred under nitrogen for 16 h. The white mixture was diluted with ether, and the dihydrochloride salt of the title compound was collected as a white solid (566 mg) by suction filtration. A portion of this material (128 mg) was partitioned between saturated aqueous sodium bicarbonate (30 mL) and ethyl acetate (30 mL). The combined organic layers were dried over sodium sulfate, filtered and concentrated to give the title compound (117 mg) as a colorless oil. Electrospray MS (positive ion): (M+H) 272

Intermediate 47

(R)-(-)-3-(Phenyloxy)-1,2-epoxypropane (U7924-89-2)

To a solution of phenol (336 mg) in anhydrous N,N-dimethylformamide (16 mL) was added sodium hydride (60% in mineral oil, 190 mg). The mixture was stirred for 1 h and (2S)-(+)-glycidyl 3-nitrobenzene sulfonate (1.0 g) in N,N-dimethylformamide (5 mL) was added. The mixture was heated to 60° C. and stirred for 30 min. The reaction was allowed to cool to room temperature, water (100 mL) was added and the mixture was extracted with 2:1 hexane:ethyl acetate (2 times 40 mL). The combined organic layers were washed with brine, dried over sodium sulfate, filtered and concentrated to supply the crude product. Purification by silica gel chromatography (eluting with 10:1 hexane: ethyl acetate) afforded the title compound (474 mg) as a colorless oil.

NMR δ values include 2.75 (dd, 1 H), 2.90 (t, 1 H), 3.35 (t, 1 H), 3.95 (dd, 1 H), 4.20 (dd, 1 H), 6.90–6.97 (m, 3 H), 7.24–7.30 (m, 2 H).

Intermediate 48

Methyl-3'-[(2-amino)ethoxy]-[1,1'-biphenyl]-3-carboxylate

The methyl-3'-[2-[[(tert-butoxy)carbonyl]amino]ethoxy]-[1,1'-biphenyl]-3-carboxylate (659 mg) was dissolved in methylene chloride (25 mL) and trifluoroacetic acid (2.5 mL) was added. The mixture was stirred at room temperature for 6 h, additional trifluoroacetic acid (1.0 mL) was added and the mixture was stirred overnight. The mixture was concentrated and partitioned between saturated aqueous sodium bicarbonate and ethyl acetate. The organic layer was separated, dried over sodium sulfate, filtered and concentrated to give the crude product. This residue was partitioned between 1:1 hexane: ethyl acetate and 1 N aqueous HCl. The aqueous layer was separated, washed with 1:1 hexane: ethyl acetate and made basic by addition of solid sodium bicarbonate. The mixture was extracted twice with ethyl acetate, and the combined organic extracts were dried over sodium sulfate, filtered and concentrated to afford the title compound (474 mg) as a colorless oil. Electrospray MS (positive ion): (M+H) 272.0.

Intermediate 49

(R)-3'-[2-[[2-(3-Chlorophenyl)-2-hydroxyethyl]amino] ethoxy]-[1,1'-biphenyl]-3-carboxylic acid methyl ester A solution of methyl-3'-[(2-amino)ethoxy]-[1,1'-biphenyl]-3-carboxylate (284.5 mg) and (R)-(-)-3-chlorostyrene oxide (124 mg) in nitromethane (4.0 mL) was heated at 70–75° C. for 20 h. The mixture was concentrated with a rotary evaporator to afford the crude product. Purification by silica gel chromatography (eluting with ethyl acetate followed by 10:1 ethyl acetate: methanol followed by 3:1 ethyl acetate: methanol) afforded the title compound (190.6 mg) as a colorless oil.

Electrospray MS (positive ion): (M+H) 425.9.

Similarly prepared was:

Intermediate 50

(R)-3'-[[2-[(2-Hydroxy-3-phenoxypropyl)amino]ethyl] amino]-[1,1'-biphenyl]-3-carboxylic acid methyl ester as a reddish oil (37 mg);

Electrospray MS (positive ion): (M+H) 421.1; from methyl-3'-[(2-aminoethyl)amino]-[1,1'-biphenyl]-3-carboxylate (117 mg) and (R)-(-)-3-(phenyloxy)-1,2-epoxypropane (54 mg).

Intermediate 51

(R)-2-(3,5-Dichlorophenyl)-2-hydroxyethanoic acid

The title compound was prepared from the corresponding cyanohydrin, which was obtained from 3,5-dichlorobenzaldehyde by a modification of the procedure employed by Huuhtranen and Kanerva for the synthesis of optically active aliphatic cyanohydrins (*Tetrahedron Asymmetry* 1992, 3, 1223). The procedure of Ziegler et al. was used to convert the cyanohydrin to the mandelic acid (*Synthesis* 1990, 575). Defatted almond meal (18.0 g, Sigma) was wetted with aqueous citrate buffer (45 mL, 0.018 M, pH 5.5). After 15 min, isopropyl ether (405 mL) was added to the moist solid, followed by 3,5-dichlorobenzaldehyde (16.07 g) and acetone cyanohydrin (24.90 mL). The mixture was then shaken at 400 rpm in a sealed flask at room temperature for 24 h. The mixture was filtered, and the almond meal was extracted with ethyl acetate. The extracts were combined with the filtrate, and concentrated to a yellow oil, which was dissolved in concentrated hydrochloric acid (27 mL). The solution was stirred at 75° C. for 4 h. The resulting thick white slurry was cooled, diluted with water (100 mL), and extracted with ether. The ether extracts were in turn extracted with 1 M aqueous sodium hydroxide solution. Acidification of the basic extracts to pH 1 (pH paper) by the dropwise addition of concentrated hydrochoric acid caused an oil to separate out of the aqueous phase. This mixture was then extracted with ether. These extracts were dried (magnesium sulfate), and concentrated to afford the title compound as an off-white crystalline solid (20.88 g).

mp: 105–106° C.

Intermediate 52

Methyl (R)-2-(3,5-dichlorophenyl)-2-hydroxyethanoate

A solution of (R)-2-(3,5-dichlorophenyl)-2-hydroxyethanoic acid (19.10 g) in methanol (200 mL) containing concentrated sulfuric acid (1 mL) was stirred at reflux under nitrogen for 16.5 h. The solution was then concentrated under vacuum, and the resulting oil was dissolved in ethyl acetate (200 mL). This solution was washed with saturated aqueous sodium bicarbonate solution, followed by saturated aqueous sodium chloride solution (10 mL). After drying (magnesium sulfate), the ethyl acetate was removed, and the yellow oil was recrystallized from hexane (70 mL) to afford the title compound as a colorless crystalline solid (10.68 g). The mother liquor afforded additional product (3.61 g) upon concentration.

mp: 68–69° C.

Intermediate 53

Methyl (R)-2-[tert-butyl(dimethyl)silyl]oxy-2-(3,5-dichlorophenyl)ethanoate

A solution of methyl (R)-2-(3,5-dichlorophenyl)-2-hydroxyethanoate (10.485 g), tert-butyidimethylsilyl chloride (8.07 g), and imidazole (3.64 g) in N,N-dimethylformamide (50 mL) was stirred under nitrogen for 18 h. Volatiles were then removed under vacuum and the residue was chromatographed on silica gel, eluting with hexanelethyl acetate (20:1) The title compound was obtained as a colorless oil (15.05 g).

Assay: Found: C 51.67, H 6.29, Cl 20.19%; $C_{15}H_{22}O_3Cl_2Si$ requires C 51.57, H 6.35, Cl 20.30%;

Intermediate 54

(R)-2-[tert-Butyl(dimethyl)silyl]oxy-2-(3,5-dichlorophenyl)ethanal

Diisobutylaluminum hydride (56.5 mL, 1.5 M in toluene) was added dropwise over 1 h to a cooled (−78° C.) solution of methyl (R)-2-[tert-butyl(dimethyl)silyl]oxy-2-(3,5-dichlorophenyl)ethanoate (14.81 g) in toluene (150 mL)

under nitrogen. The resulting colorless solution was stirred at this temperature for 1 h, before a saturated aqueous solution of Rochelle's salt (70 mL) was added dropwise. The resulting mixture was allowed to warm to room temperature, and was then diluted with ethyl acetate. The biphasic system was filtered through celite, rinsing with water and ethyl acetate . The filtrate was separated into its two layers, and the aqueous layer was extracted with ethyl acetate. The extract and the organic layer of the filtrate were combined, washed with saturated aqueous sodium chloride solution, dried (magnesium sulfate), and concentrated to afford (2R)-2-[tert-butyl(dimethyl)silyl]oxy-2-(3,5-dichlorophenyl) ethanal as a colorless oil (13.36 g). Based on its $^1$H-NMR spectrum, the title compound made up ca. 50% of the oil.

NMR δ values include 0.15 (s, 3 H), 0.21 (s, 3 H), 1.03 (s, 9 H), 5.00 (s, 1 H), 7.22–7.39 (m, 3 H), 9.56 (s, 1 H).

Intermediate 55

Methyl (R)-2-(tert-butoxycarbonyl)[2-[tert-butyl (dimethyl)silyl]oxy-2-(3,5-dichlorophenyl)ethyl] aminoacetate Glycine methyl ester hydrochloride (7.87 g) was added to a solution of crude (R)-2-[tert-butyl(dimethyl)silyl]oxy-2-(3,5-dichlorophenyl)ethanal (13.36 g) in dichloromethane (200 mL) under nitrogen. Triethylamine (8.74 mL) was then added, and the reaction mixture was stirred for 30 min. Sodium triacetoxyborohydride (17.71 g) was added, and the yellow mixture was stirred at room temperature for 22 h. The reaction mixture was then diluted with a saturated aqueous solution of Rochelle's salt (75 mL). The two layers were separated, and the cloudy aqueous phase was extracted with dichloromethane (70 mL). The extract was combined with the organic layer, washed with saturated aqueous sodium chloride (75 mL), dried (magnesium sulfate), and concentrated under vacuum to afford a yellow oil (17.10 g).

Di-tert-butyl dicarbonate (10.56 mL) was added to the yellow oil, and the resulting solution was heated at 95° C. under nitrogen for 1 h. The solution was cooled to room temperature, and chromatographed on silica gel, eluting with hexane. A colorless oil was obtained (14.221 g) that consisted of the desired product and ca. 30% (R)-2-[tert-butyl (dimethyl)silyl]oxy-2-(3,5-dichlorophenyl)-1-ethanol. In order to remove the alcohol, tert-butyldimethylsilyl chloride (2.11 g) and imidazole (953 mg) were added to a solution of the oil (14.221 g) in acetonitrile (60 mL). The reaction mixture was stirred under nitrogen for 2 h. Volatiles were then removed under vacuum, and the residue was chromatographed on silica gel, eluting with hexane/ethyl acetate (1:0 to 10:1). In this manner, a sample of the title compound was obtained containing 4% (R)-2-[tert-butyl(dimethyl)silyl] oxy-2-(3,5-dichlorophenyl)-1-ethanol (10.25 g).

Low resolution MS (ES+) 514/516 (M+Na).

Intermediate 56

(R)-[(tert-Butoxycarbonyl)-[2-(tert-butyl(dimethyl) silanyloxy)-2-(3,5-dichloro-phenylethyl]-amino]-acetaldehyde Diisobutylaluminum hydride (1.5 M in toluene, 3.9 mL) was added to methyl-(R)-2-(tert-butoxycarbonyl)-[2-(tert-butyl(dimethyl)silyl]oxy)-2-(3,5-dichlorophenyl)ethyl] amino}acetate (1.5 g) in toluene (25 mL) at −78° C. The mixture was stirred for 75 min, quenched with methanol (4 mL) followed by 15% aqueous sodium potassium tartrate (10 mL). The mixture was filtered through a pad of Celite, and the filtrate was placed in a separatory funnel after addition of ethyl acetate. The organic layer was separated, dried over sodium sulfate, filtered and concentrated to supply the title compound (1.3 g).

n.m.r. δ values include −0.13 (d, 3 H), 0.02 (d, 3 H), 0.88 (d, 9 H), 1.42 (d, 9 H), 2.9–3.2 (m, 1 H), 3.4–3.65 (m, 1 H), 3.75–4.15 (m, 2 H), 4.8–5.0 (m, 1 H), 7.05–7.35 (m,3 H), 9.50 (d, 1 H).

Intermediate 57

(R)-3'-[[2-[[2-(3-Chlorophenyl)-2-[[(tert-butyl) dimethylsilyl]oxy]ethyl][(tert-butoxy)carbonyl]amino] ethyl]amino]-[1,1'-biphenyl]-3-carboxylic acid methyl ester To a stirred solution of 3'-amino-[1,1'-biphenyl]-3-carboxylic acid methyl ester (3.0 g) and (R)-[(tert-butoxycarbonyl)-[2-(tertbutyidimethylsilanyloxy)-2-(3-chlorophenyl)ethyl]amino}acetaldehyde (8.2 g) in anhydrous dichloromethane (65 mL) was added acetic acid (8 drops). After stirring for twenty-five minutes, sodium triacetoxyborohydride (5.6 g) was added and the reaction stirred overnight. The reaction was quenched with saturated aqueous sodium bicarbonate and more dichloromethane was added. The organic layer was dried over sodium sulfate and the solvent was removed under reduced pressure to yield a white foam. The residue was purified by silica gel chromatography and eluted with 9:1 hexane:ethyl acetate to provide the title compound as a white foam (5.62 g).

Electrospray MS (positive ion): (M+H) 640.0.

Similarly prepared were:

Intermediate 58

3'-[[2R-[[2-(3-Chlorophenyl)-2R-[[(tert-butyl) dimethylsilyl]oxy]ethyl][(tert-butoxy)carbonyl]amino] propyl]amino]-[1,1'-biphenyl]-2-carboxylic acid methyl ester as a white foam (580 mg);

Electrospray MS (positive ion): (M+Na-Boc) 553; from 3'-amino-[1,1'-biphenyl]-2-carboxylic acid methyl ester (375 mg) and [2R-(tert-butoxycarbonyl)-[2R-(tert-butyldimethylsilanoxy)-2-(3-chlorophenyl)ethyl]amino]-propionaldehyde (651 mg).

Intermediate 59

3'-[[2R-[[2-(3-Chlorophenyl)-2R-[[(tert-butyl) dimethylsilyl]oxy]ethyl][(tert-butoxy)carbonyl]amino] propyl]amino]-[1,1'-biphenyl]-4-carboxylic acid methyl ester as a white foam (296 mg);

Electrospray MS (positive ion): (M+H) 653; from [2R-(tert-butoxycarbonyl)-[2R-(tert-butyldimethylsilanoxy)-2-(3-chlorophenyl)ethyl]amino]-propionaldehyde (340 mg) and 3'-amino-[1,1'-biphenyl]-4-carboxylic acid methyl ester (168 mg).

Intermediate 60

3'-[[2R-[[2-(3-Chlorophenyl)-2R-[[(tert-butyl) dimethylsilyl]oxy]ethyl][(tert-butoxyl)carbonyl]amino] propyl]amino]-[1,1'-biphenyl]-2,4-dicarboxylic acid dimethyl ester as a yellow foam (339 mg);

Electrospray MS (positive ion): (M+H) 711; from 3'-amino-[1,1'-biphenyl]-2,4-dicarboxylic acid dimethyl ester (456 mg) and [2R-(tert-butoxycarbonyl)-[2R-(tert-butyldimethylsilanoxy)-2-(3-chlorophenyl)ethyl]amino]-propionaidehyde (609 mg).

Intermediate 61

5-[3-[[2R-2-[[2-(3-Chlorophenyl)-2R-2-[[(tert-butyl) dimethylsilyl]oxy]ethyl][(tert-butoxy)carbonyl]amino] propyl]amino]phenyl]-3-pyridinecarboxylic acid methyl ester as a white foam (339 mg);

Electrospray MS (positive ion): (M+H) 654; from 5-(3-aminophenyl)-3-pyridinecarboxylic acid methyl ester (185 mg) and [2R-(tert-butoxycarbonyl)-[2R-(tert-butyldimethylsilanoxy)-2-(3-chlorophenyl)ethyl]amino]-propionaldehyde (317 mg).

Intermediate 62

2-[3-[[2R-[[2-(3-Chlorophenyl)-2R-[[(tert-butyl) dimethylsilyl]oxy]ethyl][(tert-butoxy)carbonyl]amino] propyl]amino]phenyl]-3-pyridinecarboxylic acid methyl ester as a white foam (339 mg);

Electrospray MS (positive ion): (M+H) 654; from 2-(3-aminophenyl)-3-pyridinecarboxylic acid methyl ester (273 mg) and {2R-(tert-butoxycarbonyl)-[2 R-(tert-butyldimethylsilanoxy)-2-(3-chlorophenyl)ethyl]amino}propionaldehyde (504 mg).

Intermediate 63

(R)-3'-[[2-[[2-(3-Chlorophenyl)-2-[[(tert-butyl)dimethylsilyl]oxy]ethyl][(tert-butytoxy)carbonyl]amino]ethyl]amino]-[1,1'-biphenyl]-2,4-dicarboxylic acid dimethyl ester as a foam (1.8 g);

n.m.r. δ values include –0.14 (s, 3 H), –0.01 (s, 3 H), 0.85 (s, 9 H), 1.43 (s, 9 H), 3.94 (s, 3 H), 7.41 (d, 1 H); from [3'-aminophenyl]-2,4-dicarboxylic acid dimethyl ester (1.38 g) and (R)-(tert-butoxycarbonyl)-[2-(tert-butyldimethylsilanoxy)-2-(3-chlorophenyl)ethyl]amino]-acetylaldehyde (605 mg).

Intermediate 64

(R)-3'-[[2-[[2-(3-Chlorophenyl)-2-[[(tert-butyl)dimethylsilyl]oxy]ethyl][(tert-butoxy)carbonyl]amino]ethyl]amino]-[1,1'-biphenyl]-3-chloro-4-carboxylic acid methyl ester as a foam (884 mg);

n.m.r. δ values include –0.13 (s, 3 H), 0.01 (s, 3 H), 0.86 (s, 9 H), 1.47 (s, 9 H), 3.03–3.65 (m, 6 H), 3.92 (s, 3 H), 7.88 (d, 1 H); from 3'-amino-[1,1'-biphenyl]-3-chloro4-carboxylic acid methyl ester (500 mg) and (R)-[(tert-butoxycarbonyl)-[2-(tert-butyldimethylsilanoxy)-2-(3-chlorophenyl)ethyl]amino]-acetaldehyde (1.0 g).

Intermediate 65

(R)-3'-[[2-[[2-(3-Chlorophenyl)-2-[[(tert-butyl)dimethylsilyl]oxy]ethyl][(tert-butoxy)carbonyl]amino]ethyl]amino]-[1,1'-biphenyl]-2-methyl-5-carboxylic acid methyl ester as a white foam (509 mg);

Electrospray MS (positive ion): (M+H) 653.3; from 3'-amino-[1,1'-biphenyl]-2-methyl-5-carboxylic acid methyl ester (500 mg) and {2R-(tert-butoxycarbonyl)-[2-(tert-butyldimethylsilanoxy)-2-(3-chlorophenyl)ethyl]amino}acetaldehyde (1.3 g).

Intermediate 66

(R)-5-[3-[[2-[[2-(3-Chlorophenyl)-2-[[(tert-butyl)dimethylsilyl]oxy]ethyl][(tert-butoxy)carbonyl]amino]ethyl]amino]phenyl]-2,3-dihydro-7-benzofurancarboxylic acid methyl ester as a foam (691 mg);

TLC Rf (4:1 hexane/ethyl acetate)=0.14; from 5-(3-aminophenyl)-2,3-dihydro-7-benzofurancarboxylic acid methyl ester (500 mg) and (R)-[(tert-butoxycarbonyl)-[2-(tert-butyldimethylsilanoxy)-2-(3-chlorophenyl)ethyl]amino]-acetaldehyde (1.3 g).

Intermediate 67

(R)-5-[[2-[[2-(3-Chlorophenyl)-2-[[(tert-butyl)dimethylsilyl]oxy]ethyl][(tert-butoxy)carbonyl]amino]ethyl]amino]-[phenyl]-3-pyridine-carboxylic acid ethyl ester as a yellow foam (372 mg);

Electrospray MS (positive ion): (M+H) 654.4; from 5-(3-aminophenyl)-3-pyridinecarboxylic acid ethyl ester (0.19 g) and {2R-(tert-butoxycarbonyl)-[2R-(tert-butyldimethylsilanoxy)-2-(3-chlorophenyl)ethyl]amino}acetaldehyde (0.6 g).

Intermediate 68

(R)-3'-[[2-[[2-(3-Chlorophenyl)-2-[[(tert-butyl)dimethylsilyl]oxy]ethyl][(tert-butoxy)carbonyl]amino]ethyl]amino]-[1,1'-biphenyl]-3,4-dicarboxylic acid dimethyl ester as a white foam (1.3 g);

Electrospray MS (positive ion): (M+H) 697.6; from 3'-amino-[1,1'-biphenyl]-3,4-dicarboxylic acid dimethyl ester (580 mg) and (R)-[(tert-butoxycarbonyl)-[2-(tert-butyldimethylsilanoxy)-2-(3-chlorophenyl)ethyl]amino]-acetaldehyde (1.5 g).

Intermediate 69

(R)-3'-[[2-[[2-(3,5-Dichlorophenyl)-2-[[(tert-butyl)dimethylsilyl]oxy]ethyl][(tert-butoxy)carbonyl]amino]ethyl]amino]-[1,1'-biphenyl]-3-carboxylic acid methyl ester as a white foam (1.1 g);

n.m.r. δ values include –0.12 (s, 3 H), –0.01 (s, 3 H), 0.86 (s, 9 H), 1.45 (s, 9 H), 3.92 (s, 3 H), 7.47 (t, 1 H), 7.98 (d, 1 H), 8.21 (s, 1 H); from 3'-amino-[1,1'-biphenyl]-3-carboxylic methyl ester(443 mg) and (R)-[(tert-butoxycarbonyl)-[2-(tert-butyl-dimethyl-silanyloxy)-2-(3,5-dichlorophenyl)ethyl]amino]-acetaldehyde (1.3 g).

Intermediate 70

(R)-2-[3-[[2-[[2-(3-Chlorophenyl)-2-[[(tert-butyl)dimethylsilyl]oxy]ethyl][(tert-butyloxy)carbonyl]amino]ethyl]amino]-[phenyl]-pyridine-carboxylic acid ethyl ester as a pale yellow foam (239 mg);

n.m.r. δ values include –0.12 (s, 3 H), –0.01 (s, 3 H), 0.86 (s, 9 H), 1.45 (s, 9 H), 3.92 (s, 3 H), 7.47 (t, 1 H), 7.98 (d, 1 H), 8.21 (s, 1 H); from 5-(3-aminophenyl)4-pyridinecarboxylic acid ethyl ester (216 mg) and (R)-[(tert-butoxycarbonyl)-[2-(tert-butyl-dimethyl-silanyloxy)-2-(3-chlorophenyl)ethyl]amino]-acetaldehyde (640 mg).

Intermediate 71

(R)-3'-[[2-[[2-(3-Chlorophenyl)-2-[[(tert-butyl)dimethylsilyl]oxy]ethyl][(tert-butoxy)carbonyl]amino]ethyl]amino]-[1,1'-biphenyl]-3-carbonitrile as a white foam (637 mg);

Electrospray MS (positive ion): 605.7; from 3'-amino-[1,1'-biphenyl]-3-carbonitrile (229 mg) and (R)-[(tert-butoxycarbonyl)-[2-(tert-butyldimethylsilanloxy)-2-(3-chlorophenyl)ethyl]amino]-acetaldehyde (753 mg).

Intermediate 72

(R)-6-[[2-[[2-(3-Chlorophenyl)-2-[[(tert-butyl)dimethylsilyl]oxy]ethyl][(tert-butoxy)carbonyl]amino]ethyl]amino]-[phenyl]-2-pyridine-carboxylic acid methyl ester and (R)-6-[[2-[[2-(3-chlorophenyl)-2-[[(tert-butyl)dimethylsilyl]oxy]ethyl][(tert-butoxy)carbonyl]amino]ethyl]amino]-[phenyl]-2-pyridine-carboxylic acid ethyl ester as a yellow oil (263 mg) as a 1:2.5 mixture of the methyl and ethyl esters;

Electrospray MS (positive ion ): (M+H-BOC) 539.9 and 553.9; from 6-(3-aminophenyl)-2-pyridine-carboxylic acid methyl ester, 6-(3-aminophenyl)-2-pyridinecarboxylic acid ethyl ester (126 mg), ) and (R)-[(tert-butoxycarbonyl)-[2-(tert-butyldimethylsilanloxy)-2-(3-chlorophenyl)ethyl]amino]-acetaldehyde (490 mg).

Intermediate 73

(R)-3'-[[2-[[2-(3-Chlorophenyl)-2-[[(tert-butyl)dimethylsilyl]oxy]ethyl][(tert-butoxy)carbonyl]amino]ethyl]amino]-[1,1'-biphenyl]-3-(1 H-5-tetrazole)

(A) To a stirred solution of (R)-[(tert-butoxycarbonyl)-[2-(tert-butyldimethylsilanloxy)-2-(3-chlorophenyl)ethyl]amino]-acetaldehyde (134 mg), and 3'-amino-[[1,1'-biphenyl]-3-[1 H-5-tetrazole] (50 mg) in anhydrous methanol (35 mL) was added acetic acid (45.5 mL). After stirring for 10 minutes sodium cyanoborohydride (33 mg) was added and the reaction stirred for 64 h. Worked up by partitioning between 15% Rochelle's salt and ethyl acetate. The aqueous layer was extracted again with ethyl acetate. The organic layers were combined and dried over sodium sulfate. Intermediate 74 was obtained as a white film (52 mg) after silica gel chromatography (6:1:0.1 chloroform:methanol: ammonium hydroxide);

Electrospray MS (positive ion): (M+H) 650.1

(B) To a stirred mixture of (R)-3'-[[2-[[2-(3-chlorophenyl)-2-[[(tert-butyl)dimethylsilyl]oxy]ethyl][(tert-butoxy)carbonyl]amino]ethyl]amino]-[1,1'-biphenyl]-3-carbonitrile (350 mg) and trimethylsilyl azide (134 mg) in toluene (10 mL) was added dimethyltin oxide (9.5 mg). The reaction was heated to 100° C. overnight. Methanol (5 mL)

was added, the mixture was transferred to another flask and concentrated. The mixture was partitioned between a saturated solution of sodium bicarbonate and ethyl acetate. The organic layer was extracted again with sodium bicarbonate solution and the combined aqueous layers were acidified with 3 N hydrochloric acid, extracted with ethyl acetate and the combined organic layers were dried over magnesium sulfate, filtered and concentrated to yield the crude product. Silica gel chromatography (6:1:0.1 chloroform:methanol:ammonium hydroxide) gave the title compound as a light orange foam (117 mg).

Electrospray MS (negative ion): (M-BOC-H) 547.1;
Electrospray MS (positive ion): (M-BOC+H) 549.2

Example 1

(R)-3'-[[2-[[2-(3-Chlorophenyl)-2-hydroxyethyl] amino]ethyl]amino]-[1,1'-biphenyl]-3-carboxylic acid methyl ester dihydrochloride A solution of (R)-3'-[[2-[[2-(3-chlorophenyl)-2-[[(tert-butyl)dimethylsilyl]oxy]ethyl][(tert-butoxy)carbonyl]amino]ethyl]amino]-[1,1'-biphenyl]-3-carboxylic acid methyl ester (275 mg) in 4 N hydrochloric acid in dioxane (10 mL) was stirred for 3 days. Diethyl ether was added and the reaction was stirred for 20 minutes. The title compound was collected by suction filtration as a white solid (210 mg);

$C_{24}H_{25}Cl_1N_2O_3$: MH+ calcd 425.1632, found 425.1635 Δ 0.3 mmu;

n.m.r.($CD_3OD$) δ values include 3.19–3.13 (m, 1 H), 3.36–3.30 (m, 3 H), 3.63 (t, 2 H), 3.92 (s, 3 H), 4.99 (dd, 1 H), 6.87 (d, 1 H), 7.10 (m, 2 H), 7.37–7.30 (m, 4 H), 7.47 (s, 1 H), 7.54 (t, 1 H), 7.84 (d, 1 H), 7.98 (d, 1 H), 8.22 (s, 1 H).

Similarly prepared were:

Example 2

(R)-3'-[[2-[[2-(3-Chlorophenyl)-2-hydroxyethyl] amino]ethyl]amino]-[1,1'-biphenyl]-2,4-dicarboxylic acid dimethyl ester dihydrochloride as a white solid (478 mg);

$C_{26}H_{27}Cl_1N_2O_5$: MH+ calcd 483.1687, found 483.1689 Δ 0.2 mmu;

Assay Found: C 55.95; H 5.26; N 4.98%; $C_{26}H_{27}Cl_1N_2O_5$.2HCl requires C 56.18; H 5.26; N 5.04%; from (R)-3'-[[2-[[2-(3-chlorophenyl)-2-[[(tert-butyl)dimethylsilyl]oxy]ethyl][(tert-butoxy)carbonyl]amino]ethyl]amino]-[1,1'-biphenyl]-2,4-dicarboxylic acid dimethyl ester (508 mg) in 4 N hydrochloric acid in dioxane (10 mL).

Example 3

(R)-3'-[[2-[[2-(3-chlorophenyl)-2-hydroxyethyl] amino]ethyl]amino]-[1,1'-biphenyl]-2-methyl-5-carboxylic acid methyl ester dihydrochloride as a white solid (370 mg);

Electrospray MS (positive ion): (M+H) 439.3;

n.m.r.($CD_3OD$) δ values include 2.29 (s, 3 H), 3.33 (t, 2 H), 3.57 (t, 2 H), 3.87 (s, 3 H), 4.97 (dd, 1 H), 6.72 (m, 2 H), 6.81 (d, 1 H), 7.26–7.37 (m, 5 H), 7.46 (s, 1 H), 7.80 (s,1 H), 7.86 (d, 1 H); from (R)-3'-[[2-[[2-(3-chlorophenyl)-2-[[(tert-butyl)dimethylsilyl]oxy]ethyl][(tert-butoxy)carbonyl]amino]ethyl]amino]-[1,1'-biphenyl]-2-methyl-5-carboxylic acid methyl ester (508 mg) in 4 N hydrochloric acid in dioxane (10 mL).

Example 4

(R)-3'-[[2-[[2-(3-Chlorophenyl)-2-hydroxyethyl] amino]ethyl]amino]-[1,1'-biphenyl]-3,4-dicarboxylic acid dimethyl ester dihydrochloride as a white solid (743 mg);

$C_{26}H_{27}Cl_1N_2O_5$: MH+ calcd 483.1687, found 483.1682 Δ −0.5 mmu;

Assay Found: C 55.03; H 5.36; N 5.04%; $C_{26}H_{27}Cl_1N_2O_5$.0.64$H_2O$ requires C 55.04; H 5.38; N 4.94%; from (R)-3'-[[2-[[2-(3-chlorophenyl)-2-[[(tert-butyl)dimethylsilyl]oxy]ethyl][(tert-butoxy)carbonyl]amino]ethyl]amino]-[1,1'-biphenyl]-3,4-dicarboxylic acid dimethyl ester (1.1 g) in 4 N hydrochloric acid in dioxane (10 mL).

Example 5

(R)-3'-[[2-[[2-(3-Chlorophenyl)-2-hydroxyethyl] amino]ethyl]amino]-[1,1'-biphenyl]-3-chloro-4-carboxylic acid methyl ester dihydrochloride as a white solid (617 mg);

$C_{24}H_{24}Cl_2N_2O_3$: MH+ calcd 459.1242, found 459.1235 Δ −0.7 mmu;

Assay Found: C 54.08; H 4.90; N 5.13%; $C_{24}H_{24}Cl_2N_2O_3$.2HCl requires C 54.15; H 4.92; N 5.26%; from (R)-3'-[[2-[[2-(3-chlorophenyl)-2-[[(tert-butyl)dimethylsilyl]oxy]ethyl][(tert-butoxy)carbonyl]amino]ethyl]amino]-[1,1'-biphenyl]-3-chloro-4-carboxylic acid methyl ester (874 mg) in 4 N hydrochloric acid in dioxane (10 mL).

Example 6

(R)-3'-[[2-[[2-(3-Chlorophenyl)-2-hydroxyethyl] amino]ethyl]amino]-[1,1'-biphenyl]-3-(1 H-5-tetrazole) dihydrochloride as a white solid (18.6 mg);

$C_{23}H_{23}N_6O_1Cl_1$: MH+ calcd 435.1700, found 435.1681 δ 1.9 mmu;

n.m.r. ($CD_3OD$) δ values include 3.11–3.19 (m,1 h), 3.37 (t, 2 h), 3.64 (t, 2 h), 4.99 (dd, 1 h), 6.87 (d, 1 h), 7.14–7.16 (m, 2 h), 7.32–7.34 (m, 4 h), 7.46 (s, 1 h), 7.64 (t, 1 h), 7.83 (d, 1 h), 7.96 (d, 1 h), 8.30 (s, 1 h), from (r)-3'-[[2-[[2-(3-chlorophenyl)-2-[[(tert-butyl)dimethylsilyl]oxy]ethyl][(tert-butoxy)carbonyl]amino]ethyl]amino]-[1,1'-biphenyl]-3-(1 h-5-tetrazole) (52 mg) in 4 n hydrochloric acid in dioxane (10 ml).

Example 7

(R)-3'-[[2-[[2-(3-Chlorophenyl)-2-hydroxyethyl] amino]ethyl]amino]-[1,1'-biphenyl]-3-carbonitrile dihydrochloride as a white solid (105 mg);

$C_{23}H_{22}N_3O_1Cl_1$: MH+ calcd 392.1530, found 392.1530 Δ 0.1 mmu;

Assay found: C,59.17; H, 5.19; N 8.93% $C_{23}H_{22}N_3O_1Cl_1$ 2HCl requires C, 59.43; H, 5.20; N 9.04%;

m.p. 191–206° C.; from (R)-3'-[[2-[[2-(3-chlorophenyl)-2-[[(tert-butyl)dimethylsilyl]oxy]ethyl][(tert-butoxy)carbonyl]amino]ethyl]amino]-[1,1'-biphenyl]-3-carbonitrile (173 mg) in 4 N hydrochloric acid in dioxane (10 mL).

Example 8

(R)-3'-[[2-[2-(3,5-Dichlorophenyl)-2-hydroxyethyl] amino]ethyl]amino]-[1,1'-biphenyl]-3-carboxylic acid methyl ester dihydrochioride (R)-3'-[[2-[[2-(3,5-Dichlorophenyl)-2-[[(tert-butyl) dimethylsilyl]oxy]ethyl][(tert-butoxy)carbonyl]amino]

ethyl]amino]-[1,1'-biphenyl]-3-carboxylic acid methyl ester (1.0 g) was dissolved in 4 N HCl in dioxane (10 mL) and stirred for 16 h. Addition of ether and collecting the resulting white solid gave 704 mg of a pink solid. A portion of this material (150 mg) was partitioned between ethyl acetate and saturated aqueous sodium bicarbonate, and the organic layer was separated and concentrated to give a residue that was treated with 1 N aq. HCl in ether. Concentration, dissolving in methanol/water and lyophilization gave the title compound (82 mg) as a solid.

$C_{24}H_{24}Cl_2N_2O_3$: MH+ calcd 459.1242, found 459.1224 Δ −1.8 mmu n.m.r. (DMSO-$d_6$) δ values include 3.06–3.30 (m, 4 H), 3.85 (s, 3 H), 5.01–5.04 (m, 1 H), 6.71 (d, 1 H), 6.91 (m, 2 H), 7.22 (t, 1 H), 7.42 (d, 2 H), 7.56 (m, 2 H), 7.89 (m, 2 H), 8.10 (s, 1 H).

Example 9

(R)-3'-[[2-[[2-(3,5-Dichlorophenyl)-2-hydroxyethyl] amino]ethyl]amino]-[1,1'-biphenyl]-3-carboxylic acid A crude sample of (R)-3'-[[2-[[2-(3,5-dichlorophenyl)-2-hydroxyethyl]amino]ethyl]amino]-[1,1'-biphenyl]-3-carboxylic acid methyl ester dihydrochloride (from Example 8, 557 mg), was treated with lithium hydroxide monohydrate (220 mg) in 3:1 methanol/water (28 mL) and stirred for 1 day. Additional lithium hydroxide monohydrate (22 mg) was added and the mixture was stirred overnight. The mixture was treated with 0.5 N aq. HCl until approximately pH6, and the resulting solid (400 mg) was collected by suction filtration. Silica gel chromatography (eluting with 6:2:0.1 chloroform/methanol/ammonium hydroxide) gave a solid that was triturated with hexanes. This material was treated with 1 N aqueous HCl, and the solid was washed by stirring with ethyl acetate. The solid was dried in vacuo to give the title compound (78.6 mg).

m.p. 197–201 ° C.;

$C_{23}H_{22}Cl_2N_2O_3$: MH+ calcd 445.1086, found 445.1072 Δ −1.4 mmu.

Example 10

(R)-3'-[[2-[[2-(3-Chlorophenyl)-2-hydroxyethyl] amino]ethyl]amino]-[1,1'-biphenyl]-3-carboxylic acid To a solution of the (R)-3'-[[2-[[2-(3-chlorophenyl)-2-hydroxyethyl]amino]ethyl]amino]-[1,1'-biphenyl]-3-carboxylic acid methyl ester (4.12 g) in methanol (60 mL) was added a solution of lithium hydroxide monohydrate (2.08 g) in water (20 mL). The mixture was stirred for 16 h, and 1 N hydrochloric acid was added until the mixture was neutral. The mixture was decanted and the residue was purified by flash silica chromatography eluting with 6:2:0.1 chloroform/methanol/ammonium hydroxide to afford a viscous oil. Trituration with ether and washing with water afforded the title compound as a white solid (2.22 g).

$C_{23}H_{23}Cl_1N_2O_3$: MH+ calcd 411.1475, found 411.1495 Δ 2.0 mmu;

Assay Found: C 65.90; H 5.72; N 6.70%; $C_{23}H_{23}Cl_1N_2O_3$. 0.46$H_2O$ requires C 65.90; H 5.75; N 6.68%

Similarly prepared were:

Example 11

(R)-3'-[[2-[[2-(3-Chlorophenyl)-2-hydroxyethyl] amino]ethyl]amino]-[1,1'-biphenyl]-2,4-dicarboxylic acid 2-methyl ester The product was prepared from (R)-3'-[[2-[[2-(3-chlorophenyl)-2-hydroxyethyl]amino]ethyl]amino]-[1,1'-biphenyl]-2,4-dicarboxylic acid dimethyl ester dihydrochloride (406 mg) and lithium hydroxide monohydrate (262 mg) in 3:1 methanol-water (20 mL). Silica gel chromatography eluting with 6:2:0.1 chloroform:methanol:ammonium hydroxide afforded the title compound (35 mg) as a white solid.

$C_{25}H_{25}Cl_1N_2O$: MH+ calcd 469.1530, found 469.1522 Δ −0.8 mmu;

Assay found C, 63.93, H, 5.36, N, 5.91; $C_{25}H_{25}Cl_1N_2O_5$ requires C, 64.03, H, 5.37, N. 5.97

Example 12

(R)-3'-[[2-[[2-(3-Chlorophenyl)-2-hydroxyethyl] amino]ethyl]amino]-[1,1'-biphenyl]-2,4-dicarboxylic acid Collecting the relevant fractions from further elution of the silica gel column used to provide Example 11 gave the title compound (188 mg) as a white solid.

$C_{24}H_{23}Cl_1N_2O_5$: MH+ calcd 455.1374, found 455.1377 Δ +0.3 mmu;

n.m.r. (CD$_3$OD) δ values include 3.44–3.47 (t, 2 H), 5.01 (m, 1 H), 6.61 (d, 1 H), 6.86 (d, 1 H), 6.96 (s, 1 H), 7.28–7.47 (m, 4 H), 7.46 (s, IH), 7.91 (dd, 1 H), 8.11 (d, 1 H).

Example 13

(R)-3'-[[2-[[2-(3-Chlorophenyl)-2-hydroxyethyl] amino]ethyl]amino]-[1,1'-biphenyl]-2-methyl-5-carboxylic acid as a white solid (47 mg);

$C_{24}H_{25}Cl_1N_2O_5$: MH+ calcd 425.1632, found 425.1638 Δ 0.6 mmu;

n.m.r. (DMSO-$d_6$) δ values include 2.24 (s, 3 H), 4.64 (m, IH), 5.65 (bs, 1 H), 6.43–6.45 (m, 2 H), 6.54 (d, 1 H), 7.10 (t, 1 H), 7.67 (s, 1 H), 7.74 (d, 1 H); from (R)-3'-[[2-[[2-(3-chlorophenyl)-2-hydroxyethyl]amino]ethyl]amino]-[1,1'-biphenyl]-2-methyl-5-carboxylic acid methyl ester dihydrochloride (300 mg) and lithium hydroxide monohydrate (106 mg).

Example 14

(R)-3'-[[2-[[2-(3-Chlorophenyl)-2-hydroxyethyl] amino]ethyl]amino]-[1,1'-biphenyl]-3-chloro-4-carboxylic acid as a yellow solid (205.3 mg);

$C_{23}H_{22}Cl_2N_2O$: MH+ calcd 445.1086, found 445.1071 Δ −1.5 mmu;

n.m.r. (CD$_3$OD) δ values include 3.10–3.24 (m, 1 H), 3.56 (t, 2 H), 5.00 (dd, 1 H), 4.97 (d, 1 H), 6.69 (d, 1 H), 6.90–6.92 (m, 2 H), 7.20 (t, 1 H), 7.22 (t, 3 H), 7.29–7.37 (m, 3 H), 7.42–7.50 (m, 3 H) 7.50 (d, 1 H); from (R)-3'-[[2-[[2-(3-chlorophenyl)-2-hydroxyethyl]amino]ethyl]amino]-[1, 1'-biphenyl]-3-chloro-4-carboxylic acid methyl ester dihydrochloride (500 mg) and lithium hydroxide monohydrate (158 mg).

Example 15

(R)-3'-[[2-[[2-(3-Chlorophenyl)-2-hydroxyethyl] amino]ethyl]amino]-[1,1'-biphenyl]-3,4-dicarboxylic acid as a yellow solid (205 mg);

$C_{24}H_{23}Cl_1N_2O_5$: MH+ calcd 455.1374, found 455.1390 Δ +1.6 mmu;

n.m.r. (CD$_3$OD) δ values include 2.97–3.00 (m,1 H), 3.43–3.45 (m, 2 H), 4.97 (dd, 1 H), 6.69 (d, 1 H), 6.97–6.99

(m, 2 H), 7.20–7.31 (m, 4 H), 7.42 (s, 1 H), 7.73 (d, 1 H), 8.19 (d, 1 H), 8.37 (s, 1 H); from (R)-3'-[[2-[[2-(3-chlorophenyl)-2-hydroxyethyl]amino]ethyl]amino]-[1,1'-biphenyl]-3,4-dicarboxylic acid dimethyl ester dihydrochloride (500 mg), and lithium hydroxide monohydrate (303 mg).

Example 16

(R)-3'-[[2-[(2-Hydroxy-3-phenoxypropyl)amino] ethyl]amino-[1,1'-biphenyl]-3-carboxylic acid as a yellow solid (23.2 mg);

$C_{24}H_{26}N_2O_4$: MH+ calcd 407.1971, found 407.1966 Δ +0.5 mmu;

NMR (CD$_3$OD): δ values include 3.14–3.20 (m, 1 H), 3.54 (t, 2 H), 3.95–4.04 (m, 2 H), 4.23–4.27 (m, 1 H), 6.67 (d, 1 H), 7.38 (t, 1 H), 7.62 (d, 1 H), 7.65 (d, 1 H), 7.88 (d, 1 H), 8.19 (s, 1 H); from (R)-3'-[[2-[[2-hydroxy-3-phenoxypropyl)amino]ethyl]amino]-[1,1'-biphenyl]-3-carboxylic acid methyl ester (37 mg) and lithium hydroxide monohydrate (20 mg) in 2:1 methanol: water (1 mL).

Example 17

(R)-3'-[[2-[[2-(3-Chlorophenyl)-2-hydroxyethyl] amino]ethoxy]-[1,1'-biphenyl]-3-carboxylic acid as a white solid (113.0 mg);

$C_{23}H_{22}ClNO_4$: MH+ calcd 412.1316, found 412.1308 Δ +0.8 mmu;

NMR (CD$_3$OD): δ values include 3.09–3.15 (m, 1 H), 3.45 (t, 2 H), 4.33 (t, 2 H), 4.99 (dd, H), 5.01 (s, 1 H), 6.96 (d, 1 H), 7.47 (s, 1 H), 7.65 (d, 1 H), 7.92 (d, 1 H), 8.20 (s, 1 H); from (R)-3'-[2-[[2-(3-chlorophenyl)-2-hydroxyethyl] amino]ethoxy]-[1,1'-biphenyl]-3-carboxylic acid methyl ester (190.6 mg) and lithium hydroxide monohydrate (108 mg) in 3:1 methanol: water (12 mL).

Example 18

3'-[[2R-[[2-(3-Chlorophenyl)-2R-hydroxyethyl] amino]propyl]amino]-[1,1'-biphenyl]-4-carboxylic acid A mixture of 3'-[[2R-[[2-(3-chlorophenyl)-2R-[[(tert-butyl)dimethyl]silyl]oxy]ethyl][(tert-butoxy)carbonyl] amino]propyl]amino]-[1,1'-biphenyl]-4-carboxylic acid methyl ester (289 mg) in 4 N hydrochloric acid in 1,4-dioxane (4 mL) was stirred for 1.5 h. The mixture was diluted with diethyl ether and stirred for 20 min to give a viscous residue. The solvent was decanted from the residue and the residue was dried under vacuum. This material was dissolved in 3:1 methanol:water (10 mL), treated with lithium hydroxide monohydrate (120 mg) and stirred overnight. The mixture was concentrated under reduced pressure and chromatographed on silica eluting with methanol:dichloromethane:88% ammonium hydroxide (15:85:1.5) to give the title compound as a white solid (31 mg).

Electrospray MS (positive ion): (M+H) 425;

HPLC (C18): 98.35% purity, 12.7 minute retention time using a 10–100% acetonitrile-water with 0.1% trifluoroacetic acid.

Examples 19–25 were prepared in a similar manner as in Example 18.

Example 19

3'-[[2R-[[2-(3-Chlorophenyl)-2R-hydroxyethyl] amino]propyl]amino]-[1,1'-biphenyl]-2-carboxylic acid as a white solid (238 mg), Electrospray MS (positive ion): (M+H) 425

HPLC (C18): 95.5% purity, 11.8 minute retention time using a 30–80% acetonitrile-water with 0.1% trifluoroacetic acid gradient mobile phase with detection by absorbance at 254 nM:. from 3'-[[2R-[[2-(3-chlorophenyl)-2R-[[(tert-butyl)dimethylsilyl]oxy]ethyl][(tert-butoxy)carbonyl] amino]propyl]amino]-[1,1'-biphenyl]-2-carboxylic acid methyl ester (575 mg), 4 N hydrochloric acid in 1,4-dioxane (5 mL) and lithium hydroxide monohydrate (1 85 mg) in 3:1 methanol-water (10 mL).

Example 20

3'-[[2R-[[2-(3-Chlorophenyl)-2R-hydroxyethyl] amino]propyl]amino]-[1,1'-biphenyl]-2,4-dicarbonylic acid as a yellow solid (302 mg);

Electrospray MS (positive ion): (M+H) 469

HPLC (C18): 94.2% purity, 8.71 minute retention time using a 30–80% acetonitrile-water with 0.1% trifluoroacetic acid gradient mobile phase with detection by absorbance at 254 nM; from 3'-[[2R-[[2-(3-chlorophenyl)-2R-[[(tert-butyl)dimethylsilyl]oxy]ethyl][(tert-butoxy)carbonyl] amino]propyl amino]-[1,1'-biphenyl]-2,4-dicarboxylic acid dimethyl ester (655 mg), 4 N hydrochloric acid in 1,4-dioxane (5 mL) and lithium hydroxide monohydrate (256 mg) in 3:1 methanol-water (4 mL).

Example 21

5-[3-[[2R-[[2-(3-Chlorophenyl)-2R-hydroxyethyl] amino]propyl]amino]phenyl]-3-pyridinecarboxylic acid as a yellow solid (111 mg);

Electrospray MS (positive ion): (M+H) 426

HPLC (C18): 94.0% purity, 6.30 minute retention time using a 30–80% acetonitrile-water with 0.1% trifluoroacetic acid gradient mobile phase with detection by absorbance at 254 nM; from 5-[3-[[2R-[[2-(3-chlorophenyl)-2R -[[(tert-butyl)dimethylsilyl]oxy]ethyl][(tert-butoxy)carbonyl] amino]propyl]amino]phenyl]-3-pyridinecarboxylic acid methyl ester (292 mg), 4 N hydrochloric acid in 1,4-dioxane (5 mL) and lithium hydroxide monohydrate (65 mg) in 3:1 tetrahydrofuran-water (3 mL).

Example 22

2-[3-[[2R-[[2-(3-Chlorophenyl)-2R-hydroxyethyl] amino]propyl]amino]phenyl]-3-pyridinecarboxylic acid as a yellow solid (268 mg);

Electrospray MS (positive ion): (M+H) 426;

HPLC (C18): 95.5% purity, 4.79 minute retention time using a 30–80% acetonitrile-water with 0.1% trifluoroacetic acid gradient mobile phase with detection by absorbance at 254 nM; from 2-[3-[[2R-[[2-(3-chlorophenyl)-2R-[[(tert-butyl)dimethylsilyl]oxy]ethyl][(tert-butoxy)-carbonyl] amino]propyl]amino]phenyl]-3-pyridinecarboxylic acid methyl ester (420 mg), 4 N hydrochloric acid in 1,4-dioxane (4 mL) and lithium hydroxide monohydrate (295 mg) in 3:1 tetrahydrofuran-water (3 mL).

Example 23

(R)-5-[3-[[2-[[2-(3-chlorophenyl)-2-hydroxyethyl] amino]ethyl]amino]phenyl-2,3-dihydro-7-benzofurancarboxylic acid as a yellow solid (197 mg);

$C_{25}H_{25}Cl_1N_2O_4$: MH+ calcd 453.1581, found 453.1569 Δ −1.2 mmu;

Assay found C, 61.04, H, 5.37, N, 5.60; $C_{25}H_{25}Cl_1N_2O_4 \cdot 0.67LiCl \cdot 0.59H_2O$ requires C, 61.04, H, 5.36, N, 5.69; from (R)-5-[3-[[2-[[2-(3-chlorophenyl)-2-[[(tert-butyl)dimethylsilyl]oxy]ethyl][(tert-butoxy)carbonyl]amino]ethyl]amino]phenyl]-2,3-dihydro-7-benzofurancarboxylic acid methyl ester (691 mg), 4 N hydrochloric acid in 1,4-dioxane (10 mL) and lithium hydroxide monohydrate (170 mg) in 3:1 tetrahydrofuran-water (20 mL).

Example 24

(R)-5-[3-[[2-[[2-(3-chlorophenyl)-2-hydroxyethyl]amino]ethyl]amino]phenyl]-3-pyridinecarboxylic acid as a yellow solid (115 mg);

$C_{22}H_{22}Cl_1N_3O_3$: MH+ calcd 412.1428, found 412.1425 Δ −0.3 mmu;

n.m.r. ($CD_3OD$) δ values include 3.11–3.29 (m, 1 H), 3.58 (t, 2 H), 4.97 (dd, 1 H), 6.76 (d, 1 H), 6.97 (s, 1 H), 6.99 (d, 1 H), 7.26–7.35 (m, 4 H), 7.46 (s, 1 H), 8.51 (s, 1 H), 8.76 (s, 1 H), 9.00 (s, 1 H); from (R)-5-[3-[[2-[[2-(3-chlorophenyl)-2-[[(tert-butyl)dimethylsilyl]oxy]ethyl][(tert-butoxy)carbonyl]amino]ethyl]amino]phenyl]-3-pyridinecarboxylic acid methyl ester (251 mg), 4 N hydrochloric acid in 1,4-dioxane (10 mL) and lithium hydroxide monohydrate (96 mg) in 3:1 tetrahydrofuran-water (20 mL).

Example 25

(R)-2-[3-[[2-[[2-(3-chlorophenyl)-2-hydroxyethyl]amino]ethyl]amino]phenyl[-4-pyridinecarboxylic acid as a yellow solid (52 mg);

Electrospray MS (positive ion): (M+H) 412.1;

n.m.r. ($CD_3OD$) δ values include 3.11–3.17 (m, 1 H), 3.58 (t, 2 H), 4.96 (dd, 1 H), 7.46 (s, 1 H), 7.75 (d, 1 H), 8.21 (s, 1 H), 8.59 (d, 1 H); from (R)-3'-[[2-[[2-(3-chlorophenyl)-2-[[(tert-butyl)dimethylsilyl]oxy]ethyl][(tert-butoxy)carbonyl]amino]ethyl]amino]-[phenyl]-4-pyridinecarboxylic acid ethyl ester (239 mg), 4 N hydrochloric acid in 1,4-dioxane (10 mL) and lithium hydroxide monohydrate (55 mg) in 3:1 tetrahydrofuran-water (15.5 mL).

Example 26

(R)-6-[3-[[2-[[2-(3-chlorophenyl)-2-hydroxyethyl]amino]ethyl]amino]phenyl]-2-pyridinecarboxylic acid as a yellow solid (30 mg);

$C_{22}H_{22}N_3O_3Cl$: MH+ calcd. 412.1428, found 412.1436 Δ +0.9mmu;

n.m.r. ($CD_3OD$) δ values include 3.24–3.08 (m, 2 H), 3.61 (t, 2 H), 5.01 (dd, 1 H), 6.72 (d, 1 H), 7.44 (s, 1 H), 7.65 (s, 1 H), 7.96–7.86 (m, 3 H); from a 2.5:1 mixture of (R)-6-[3-[[2-[[2-(3-chlorophenyl)-2-[[(tert-butyl)dimethylsilyl]oxy]ethyl][(tert-butoxy)carbonyl]amino]ethyl]amino]phenyl]-2-pyridinecarboxylic acid methyl ester and (R)-6-[3-[[2-[[2-(3-chlorophenyl)-2-[[(tert-butyl)dimethylsilyl]oxy]ethyl][(tert-butoxy)carbonyl]amino]ethyl]amino]phenyl]-2-pyridinecarboxylic acid ethyl ester (263 mg), 4 N hydrochloric acid in dioxane (10 mL) and lithium hydroxide monohydrate (65 mg) in (3:1) methanol: water (40 mL) The intermediate ester (170 mg) was isolated by column chromatography ( eluting with 12:1:0.1 chloroform:methanol:ammonium hydroxide).

Tablet compositions

The following compositions A and B can be prepared by wet granulation of ingredients (a) to (c) and (a) to (d) with a solution of povidone, followed by addition of the magnesium stearate and compression.

Composition A

| | | mg/tablet | mg/tablet |
|---|---|---|---|
| (a) | Active ingredient | 250 | 250 |
| (b) | Lactose B.P. | 210 | 26 |
| (c) | Sodium Starch Glycollate | 20 | 12 |
| (d) | Povidone B.P. | 15 | 9 |
| (e) | Magnesium Stearate | 5 | 3 |
| | | 500 | 300 |

Composition B

| | | mg/tablet | mg/tablet |
|---|---|---|---|
| (a) | Active ingredient | 250 | 250 |
| (b) | Lactose 150 | 150 | — |
| (c) | Avicel PH 101 | 60 | 26 |
| (d) | Sodium Starch Glycollate | 20 | 12 |
| (e) | Povidone B.P. | 15 | 9 |
| (f) | Magnesium Stearate | 5 | 3 |
| | | 500 | 300 |

Composition C

| | mg/tablet |
|---|---|
| Active ingredient | 100 |
| Lactose | 200 |
| Starch | 50 |
| Povidone | 5 |
| Magnesium Stearate | 4 |

The following compositions D and E can be prepared by direct compression of the admixed ingredients. The lactose used in composition E is of the direct compression type.

Composition D

| | mg/tablet |
|---|---|
| Active ingredient | 250 |
| Magnesium Stearate | 4 |
| Pregelatinised Starch NF15 | 146 |
| | 400 |

Composition E

| | mg/tablet |
|---|---|
| Active ingredient | 250 |
| Magnesium Stearate | 5 |
| Lactose | 145 |
| Avicel | 100 |
| | 500 |

Composition F (Controlled release composition)

| | | mg/tablet |
|---|---|---|
| (a) | Active ingredient | 500 |
| (b) | Hydroxypropylmethylcellulose (Methocel K4M Premium) | 112 |
| (c) | Lactose B.P. | 53 |
| (d) | Povidone B.P.C. | 28 |
| (e) | Magnesium Stearate | 7 |
| | | 700 |

The composition can be prepared by wet granulation of ingredients (a) to (c) with a solution of povidone, followed by addition of the magnesium stearate and compression.

Composition G (Enteric-coated tablet)

Enteric-coated tablets of Composition C can be prepared by coating the tablets with 25 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

Composition H (Enteric-coated controlled release tablet)

Enteric-coated tablets of Composition F can be prepared by coating the tablets with 50 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

Capsule compositions

Composition A

Capsules can be prepared by admixing the ingredients of Composition D above and filling two-part hard gelatin capsules with the resulting mixture. Composition B (infra) may be prepared in a similar manner.

Composition B

| | | mg/capsule |
|---|---|---|
| (a) | Active ingredient | 250 |
| (b) | Lactose B.P. | 143 |
| (c) | Sodium Starch Glycollate | 25 |
| (d) | Magnesium Stearate | 2 |
| | | 420 |

Composition C

| | | mg/capsule |
|---|---|---|
| (a) | Active ingredient | 250 |
| (b) | Macrogol 4000 BP | 350 |
| | | 600 |

Capsules can be prepared by melting the Macrogol 4000 BP, dispersing the active ingredient in the melt and filling two-part hard gelatin capsules therewith.

Composition D

| | mg/capsule |
|---|---|
| Active ingredient | 250 |
| Lecithin | 100 |
| Arachis Oil | 100 |
| | 450 |

Capsules can be prepared by dispersing the active ingredient in the lecithin and arachis oil and filling soft, elastic gelatin capsules with the dispersion.

Composition E (Controlled release capsule)

| | | mg/capsule |
|---|---|---|
| (a) | Active ingredient | 250 |
| (b) | Microcrystalline Cellulose | 125 |
| (c) | Lactose BP | 125 |
| (d) | Ethyl Cellulose | 13 |
| | | 513 |

The controlled release capsule composition can be prepared by extruding mixed ingredients (a) to (c) using an extruder, then spheronising and drying the extrudate. The dried pellets are coated with a release controlling membrane (d) and filled into two-part, hard gelatin capsules.

Composition F (Enteric capsule)

| | | mg/capsule |
|---|---|---|
| (a) | Active ingredient | 250 |
| (b) | Microcrystalline Cellulose | 125 |
| (c) | Lactose BP | 125 |

Composition F (Enteric capsule) -continued

| | | mg/capsule |
|---|---|---|
| (d) | Cellulose Acetate Phthalate | 50 |
| (e) | Diethyl Phthalate | 5 |
| | | 555 |

The enteric capsule composition can be prepared by extruding mixed ingredients (a) to (c) using an extruder, then spheronising and drying the extrudate. The dried pellets are coated with an enteric membrane (d) containing a plasticizer (e) and filled into two-part, hard gelatin capsules.

Composition G (Enteric-coated controlled release capsule)

Enteric capsules of Composition E can be prepared by coating the controlled-release pellets with 50 mg/capsule of an enteric polymer such as cellulose acetate phthalate, polyvinylacetate phthalate, hydroxypropylmethylcellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

| Intravenous injection composition | |
|---|---|
| Active ingredient | 0.200 g |
| Sterile, pyrogen-free phosphate buffer (pH 9.0) to | 10 ml |

The active ingredient is dissolved in most of the phosphate buffer at 35–40° C., then made up to volume and filtered through a sterile micropore filter into sterile 10 ml glass vials (Type 1) which are sealed with sterile closures and overseals.

| Intramuscular injection composition | |
|---|---|
| Active ingredient | 0.20 g |
| Benzyl Alcohol | 0.10 g |
| Glycofurol 75 | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (Type 1).

| Syrup composition | |
|---|---|
| Active ingredient | 0.25 g |
| Sorbitol Solution | 1.50 g |
| Glycerol | 1.00 g |
| Sodium Benzoate | 0.005 g |
| Flavour | 0.0125 ml |
| Purified Water q.s. to | 5.0 ml |

The sodium benzoate is dissolved in a portion of the purified water and the sorbitol solution added. The active ingredient is added and dissolved. The resulting solution is mixed with the glycerol and then made up to the required volume with the purified water.

| Suppository composition | |
|---|---|
| | mg/suppository |
| Active ingredient | 250 |
| Hard Fat, BP (Witepsol H15 - Dynamit NoBel) | 1770 |
| | 2020 |

One-fifth of the Witepsol H15 is melted in a steam-jacketed pan at 45° C. maximum. The active ingredient is sifted through a 200 lm sieve and added to the molten base with mixing, using a Silverson fitted with a cutting head, until a smooth dispersion is achieved. Maintaining the mixture at 45° C., the remaining Witepsol H15 is added to the suspension which is stirred to ensure a homogenous mix. The entire suspension is then passed through a 250 lm stainless steel screen and, with continuous stirring, allowed to cool to 40° C. At a temperature of 38–40° C., 2.02 g aliquots of the mixture are filled into suitable plastic moulds and the suppositories allowed to cool to room temperature.

| Pessary composition | |
|---|---|
| | mg/pessary |
| Active ingredient (63 lm) | 250 |
| Anhydrous Dextrose | 380 |
| Potato Starch | 363 |
| Magnesium Stearate | 7 |
| | 1000 |

The above ingredients are mixed directly and pessaries prepared by compression of the resulting mixture.

| Transdermal composition | |
|---|---|
| Active ingredient | 200 mg |
| Alcohol USP | 0.1 ml |
| Hydroxyethyl cellulose | |

The active ingredient and alcohol USP are gelled with hydroxyethyl cellulose and packed in a transdermal device with a surface area of 10 cm².

What is claimed is:

1. A compound of Formula (I) or a pharmaceutically acceptable derivative thereof:

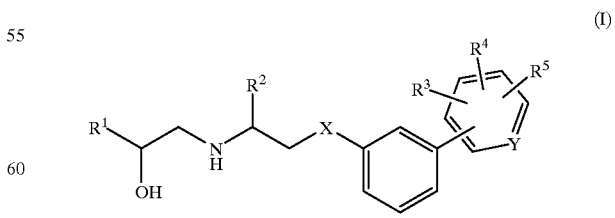

(I)

wherein $R^1$ is a phenyl, naphthyl, pyridyl, thiazolyl, phenoxymethyl, or pyrimidyl group, optionally substituted by one or more substituents selected from the group consisting of halogen, hydroxy, $C_{1-6}$alkoxy, $C_{1-6}$alkyl, nitro, cyano, hydroxymethyl, trifluoromethyl, —NR$^6$R$^6$, and —NHSO$_2$R$^6$, where each R$^6$ is independently hydrogen or C$_{1-4}$alkyl;

R$^2$ is hydrogen or C$_{1-6}$alkyl;

X is oxygen, sulfur, —NH, or —NC$_{1-4}$alkyl;

R$^3$ is cyano, tetrazol-5-yl, or -CO$_2$R$^7$ where R$^7$ is hydrogen or C$_{1-6}$alkyl;

R$^4$ and R$^5$ are independently hydrogen, C$_{1-6}$alkyl, —CO$_2$H, —CO$_2$C$_{1-6}$alkyl, cyano, tetrazol-5-yl, halogen, trifluoromethyl, or C$_{1-6}$alkoxy, or, when R$^4$ and R$^5$ are bonded to adjacent carbon atoms, R$^4$ and R$^5$ may, together with the carbon atoms to which they are bonded, form a fused 5 or 6 membered ring optionally containing one or two nitrogen, oxygen, or sulfur atoms; and Y is N or CH.

2. A compound according to claim 1 wherein R$^1$ is phenoxymethyl or phenyl optionally substituted by one, two, or three substituents selected from halogen, hydroxy, C$_{1-6}$alkoxy, C$_{1-6}$alkyl, nitro, cyano, hydroxymethyl, and trifluoromethyl.

3. A compound according to claim 1 wherein R$^1$ is phenoxymethyl or phenyl substituted by a chlorine, fluorine, bromine, methyl, or trifluoromethyl.

4. A compound according to claim 1 wherein R$^2$ is hydrogen or methyl.

5. A compound according to claim 1 wherein R$^2$ is hydrogen.

6. A compound according to claim 1 wherein X is NH.

7. A compound according to claim 1 wherein R$^3$ is CO$_2$H.

8. A compound according to claim 1 wherein at least one of R$^4$ and R$^5$ is hydrogen.

9. A compound according to claim 1 wherein R$^4$ and R$^5$ are both hydrogen.

10. A compound according to claim 1 wherein Y is CH.

11. A compound according to claim 1 wherein R$^1$ is phenoxymethyl or phenyl substituted by a chlorine, fluorine, bromine, methyl, or trifluoromethyl; R$^2$ is hydrogen or methyl; X is NH, or NCH$_3$; R$^3$ is CO$_2$H; and Y is CH.

12. A compound selected from the group consisting of:
(R)-3'-[[2-[[2-(3-chlorophenyl)-2-hydroxyethyl]amino]ethyl]amino]-[1,1'-biphenyl]-3-carboxylic acid methyl ester;
(R)-3'-[[2-[[2-(3-chlorophenyl)-2-hydroxyethyl]amino]ethyl]amino]-[1,1'-biphenyl]-2,4-dicarboxylic acid dimethyl ester;
(R)-3'-[[2-[[2-(3-chlorophenyl)-2-hydroxyethyl]amino]ethyl]amino]-[1,1'-biphenyl]-2-methyl-5-carboxylic acid methyl ester;
(R)-3'-[[2-[[2-(3-chlorophenyl)-2-hydroxyethyl]amino]ethyl]amino]-[1,1'-biphenyl]-3,4-dicarboxylic acid dimethyl ester;
(R)-3'-[[2-[[2-(3-chlorophenyl)-2-hydroxyethyl]amino]ethyl]amino]-[1,1'-biphenyl]-3-chloro-4-carboxylic acid methyl ester;
(R)-3'-[[2-[[2-(3,5-dichlorophenyl)-2-hydroxyethyl]amino]ethyl]amino]-[1,1'-biphenyl]-3-carboxylic acid methyl ester;
(R)-3'-[[2-[[2-(3,5-dichlorophenyl)-2-hydroxyethyl]amino]ethyl]amino]-[1,1'-biphenyl]-3-carboxylic acid;
(R)-3'-[[2-[[2-(3-chlorophenyl)-2-hydroxyethyl]amino]ethyl]amino]-[1,1'-biphenyl]-3-carboxylic acid;
(R)-3'-[[2-[[2-(3-chlorophenyl)-2-hydroxyethyl]amino]ethyl]amino]-[1,1'-biphenyl]-2,4-dicarboxylic acid 2-methyl ester;
(R)-3'-[[2-[[2-(3-chlorophenyl)-2-hydroxyethyl]amino]ethyl]amino]-[1,1'-biphenyl]-2,4-dicarboxylic acid;
(R)-3'-[[2-[[2-(3-chlorophenyl)-2-hydroxyethyl]amino]ethyl]amino]-[1,1'-biphenyl]-2-methyl-5-carboxylic acid;
(R)-3'-[[2-[[2-(3-chlorophenyl)-2-hydroxyethyl]amino]ethyl]amino]-[1,1'-biphenyl]-3-chloro-4-carboxylic acid;
(R)-3'-[[2-[[2-(3-chlorophenyl)-2-hydroxyethyl]amino]ethyl]amino]-[1,1'-biphenyl]-3,4-dicarboxylic acid;
(R)-3'-[[2-[(2-hydroxy-3-phenoxypropyl)amino]ethyl]amino-[1,1'-biphenyl]-3-carboxylic acid;
(R)-3'-[[2-[[2-(3-chloropheny)-2-hydroxyethyl]amino]ethoxy]-1,1'-biphenyl]-3-carboxylic acid;
3'-[[2R-[[2-(3-chlorophenyl)-2R-hydroxyethyl]amino]propyl]amino]-[1,1'-biphenyl]-4-carboxylic acid;
3'-[[2R-[[2-(3-chlorophenyl)-2R-hydroxyethyl]amino]propyl]amino]-[1,1'-biphenyl]-2-carboxylic acid;
3'-[[2R-[[2-(3-chlorophenyl)-2R-hydroxyethyl]amino]propyl]amino]-[1,1'-biphenyl]-2,4-dicarboxylic acid;
5-[3-[[2R-[[2-(3-chlorophenyl)-2R-hydroxyethyl]amino]propyl]amino]phenyl]-3-pyridinecarboxylic acid;
2-[3-[[2R-[[2-(3-chlorophenyl)-2R-hydroxyethyl]amino]propyl]amino]phenyl]-3-pyridinecarboxylic acid;
(R)-5-[3-[[2-[[2-(3-chlorophenyl)-2-hydroxyethyl]amino]ethyl]amino]phenyl]-2,3-dihydro-7-benzofurancarboxylic acid;
(R)-5-[3-[[2-[[2-(3-chlorophenyl)-2-hydroxyethyl]amino]ethyl]amino]phenyl]-3-pyridinecarboxylic acid;
(R)-2-[3-[[2-[[2-(3-chlorophenyl)-2-hydroxyethyl]amino]ethyl]amino]phenyl]-4-pyridinecarboxylic acid;
(R)-3'-[[2-[[2-(3-chlorophenyl)-2-hydroxyethyl]amino]ethyl]amino]-[1,1'-biphenyl]-3-(1 H-5-tetrazole);
(R)-3'-[[2-[[2-(3-chlorophenyl)-2-hydroxyethyl]amino]ethyl]amino]-[1,1'-biphenyl]-3-carbonitrile;
(R)-2-[3-[[2-[[2-(3-chlorophenyl)-2-hydroxyethyl]amino]ethyl]amino]phenyl]-2-pyridinecarboxylic acid;
or a pharmaceutically acceptable derivative thereof.

13. A compound selected from the group consisting of:
(R)-5-(3-[[2-[[2-(3-chlorophenyl)-2-hydroxyethyl]amino]ethyl]amino]phenyl]-3-pyridinecarboxylic acid;
3'-[[2R-[[2-(3-chlorophenyl)-2R-hydroxyethyl]amino]propyl]amino]-[1,1'-biphenyl]-2,4-dicarboxylic acid;
(R)-3'-[[2-[(2-hydroxy-3-phenoxypropyl)amino]ethyl]amino-[1,1'-biphenyl]-3-carboxylic acid;
(R)-3'-[[2-[[2-(3-chlorophenyl)-2-hydroxyethyl]amino]ethyl]amino]-[1,1'-biphenyl]-2-methyl-5-carboxylic acid;
(R)-3'-[[2-[[2-(3-chlorophenyl)-2-hydroxyethyl]amino]ethyl]amino]-[1,1'-biphenyl]-3-carboxylic acid;
or a pharmaceutically acceptable derivative thereof.

14. A method for the treatment of a mammal of conditions susceptible of amelioration by an atypical beta-adrenoceptor agonist comprising administration of an effective amount of a compound according to claim 1 or a pharmaceutically acceptable salt thereof.

15. A pharmaceutical composition comprising a compound according to claim 1, or a pharmaceutically acceptable salt thereof, together with one or more pharmaceutically acceptable carriers.

16. A process for the preparation of a compound of formula (I) or a pharmaceutically acceptable derivative thereof:

(I)

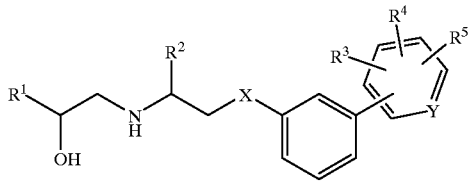

wherein R¹ is a phenyl, naphthyl, pyridyl, thiazolyl, phenoxymethyl, or pyrimidyl group, optionally substituted by one or more substituents selected from the group consisting of halogen, hydroxy, $C_{1-6}$alkoxy, $C_{1-6}$alkyl, nitro, cyano, hydroxymethyl, trifluoromethyl, —NR⁶R⁶, and —NHSO₂R⁶, where each R⁶ is independently hydrogen or $C_{1-4}$alkyl;

R² is hydrogen or $C_{1-6}$alkyl;

X is oxygen, sulfur, —NH, or —N$C_{1-4}$alkyl;

R³ is cyano, tetrazol-5-yl, or —CO₂R⁷ where R⁷ is hydrogen or $C_{1-6}$alkyl;

R⁴ and R⁵ are independently hydrogen, $C_{1-6}$alkyl, —CO₂H, —CO₂$C_{1-6}$alkyl, cyano, tetrazol-5-yl, halogen, trifluoromethyl, or $C_{1-6}$alkoxy, or, when R⁴ and R⁵ are bonded to adjacent carbon atoms, R⁴ and R⁵ may, together with the carbon atoms to which they are bonded, form a fused 5 or 6 membered ring optionally containing one or two nitrogen, oxygen, or sulfur atoms; and Y is N or CH said process comprising:

(A) deprotection of a compound of Formula (II), (II)

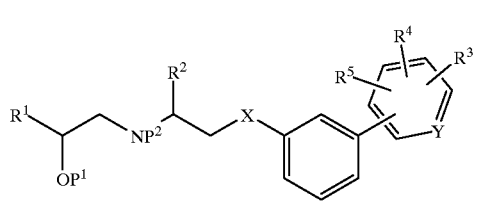

wherein P¹ is a suitable protecting group for oxygen and P² is a suitable protecting group for nitrogen or;

(B) interconversion of another compound of Formula (I); or (C) reaction of compound of Formula (III) with a compound of Formula (IV), followed by step (A) without purification of intermediate products;

(III)

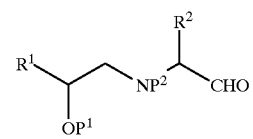

(IV)

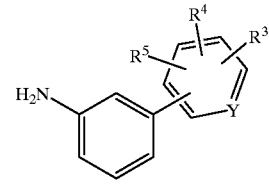

or (D) reaction of a compound of Formula (VIII) with a compound of Formula (IX)

(VIII)

(IX)

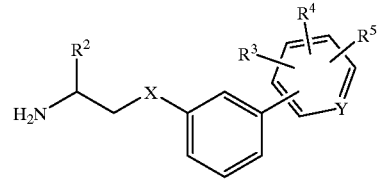

17. The method according to claim 14 wherein said mammal is man.

* * * * *

UNITED STATES PATENT AND TRADEMARK OFFICE
Certificate

Patent No. 6,251,925 B1                               Patented: June 26, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Kelly Horne Donaldson, Durham, NC (US); Barry George Shearer, Apex, NC (US); David Edward Uehling, Durham, NC (US); and David Norman Deaton, Durham, NC (US).

Signed and Sealed this Third Day of July 2007.

WILLIAM R. DIXON, JR.
*Special Program Examiner*
Technology Center 1600